(12) United States Patent
Ishida et al.

(10) Patent No.: US 10,975,206 B2
(45) Date of Patent: Apr. 13, 2021

(54) POLAR SOLVENT SOLUTION AND PRODUCTION METHOD THEREOF

(71) Applicant: SPIBER INC., Tsuruoka (JP)

(72) Inventors: Kana Ishida, Yamagata (JP); Hironori Yamamoto, Yamagata (JP); Hiroaki Suzumura, Yamagata (JP); Kazuhide Sekiyama, Yamagata (JP)

(73) Assignee: SPIBER INC., Yamagata (JP)

( * ) Notice: Subject to any disclaimer, the term of this patent is extended or adjusted under 35 U.S.C. 154(b) by 0 days.

(21) Appl. No.: 15/564,373

(22) PCT Filed: Apr. 4, 2016

(86) PCT No.: PCT/JP2016/061026
§ 371 (c)(1),
(2) Date: Oct. 4, 2017

(87) PCT Pub. No.: WO2016/163337
PCT Pub. Date: Oct. 13, 2016

(65) Prior Publication Data
US 2018/0127553 A1 May 10, 2018

(30) Foreign Application Priority Data
Apr. 9, 2015 (JP) .............................. JP2015-080231

(51) Int. Cl.
*C08J 3/09* (2006.01)
*C07K 1/14* (2006.01)
(Continued)

(52) U.S. Cl.
CPC ................. *C08J 3/097* (2013.01); *C07K 1/14* (2013.01); *C07K 14/435* (2013.01); *C08L 89/00* (2013.01);
(Continued)

(58) Field of Classification Search
CPC .. C07K 1/14; C07K 14/435; C07K 14/43518; C07K 14/00; C08J 3/097; C08J 2389/00;
(Continued)

(56) References Cited

U.S. PATENT DOCUMENTS

| 5,171,505 A | 12/1992 | Lock |
| 5,252,284 A | 10/1993 | Lock |

(Continued)

FOREIGN PATENT DOCUMENTS

| CN | 1078509 | 11/1993 |
| CN | 1774241 | 5/2006 |

(Continued)

OTHER PUBLICATIONS

Kiyoichi Matsumoto, et al., "Regenerated Protein Fibers. I. Research and Development of a Novel Solvent for Silk Fibroin", Journal of Polymer Science, Part A: Polymer Chemistry, vol. 35, No. 10, Jul. 30, 1997, pp. 1949-1954.

(Continued)

*Primary Examiner* — Patricia L. Hailey
(74) *Attorney, Agent, or Firm* — Hamre, Schumann, Mueller & Larson, P.C.

(57) ABSTRACT

A polar solvent solution of the present invention is a polar solvent solution in which a solute containing a polyamine acid is dissolved in a polar solvent. An inorganic salt is added to the solution, and a mole ratio of moisture to the inorganic salt in the solution is 2.5×m×n or less, where m represents the number of cations forming the inorganic salt and n represents a charge number of the cation. A production method of the present invention is a method for producing the above solution, including: changing at, least one of a moisture content and a content of the inorganic salt in the solution to adjust a viscosity of the solution. Thus, the present invention provides a polar solvent solution whose (Continued)

viscosity can be easily adjusted to a desired value and thus enables stable spinning and casting when used as dopes for spinning, film, etc., and methods for producing the same.

9 Claims, 4 Drawing Sheets

Specification includes a Sequence Listing.

(51) Int. Cl.

| | |
|---|---|
| C07K 14/435 | (2006.01) |
| C08L 89/00 | (2006.01) |
| D01F 1/10 | (2006.01) |
| D01F 4/02 | (2006.01) |
| C07K 14/00 | (2006.01) |

(52) U.S. Cl.
CPC .............. *D01F 1/10* (2013.01); *D01F 4/02* (2013.01); *C07K 14/00* (2013.01); *C08J 2389/00* (2013.01); *C08L 2203/16* (2013.01)

(58) Field of Classification Search
CPC ........ C08L 89/00; C08L 2203/16; D01F 1/10; D01F 4/02
USPC .............. 106/154.11, 154.3, 124.4; 530/858
See application file for complete search history.

(56) References Cited

U.S. PATENT DOCUMENTS

| | | | |
|---|---|---|---|
| 5,736,586 A | 4/1998 | Bastioli et al. | |
| 6,620,917 B1 | 9/2003 | Mello et al. | |
| 7,014,802 B1 | 3/2006 | Eby et al. | |
| 7,057,023 B2 | 6/2006 | Islam et al. | |
| 7,226,618 B1* | 6/2007 | Touraud | A61K 9/5138 424/489 |
| 7,335,739 B2 | 2/2008 | Mello et al. | |
| 8,278,416 B1 | 10/2012 | Johansson et al. | |
| 8,568,637 B2 | 10/2013 | Gazit et al. | |
| 9,051,453 B2* | 6/2015 | Sugahara | D01D 5/04 |
| 9,689,089 B2 | 6/2017 | Ishikawa | |
| 2003/0155670 A1 | 8/2003 | O'Brien | |
| 2003/0201560 A1 | 10/2003 | Vollrath et al. | |
| 2004/0102614 A1 | 5/2004 | Islam et al. | |
| 2004/0132957 A1 | 7/2004 | Asakura | |
| 2004/0161382 A1 | 8/2004 | Yum et al. | |
| 2005/0054830 A1 | 3/2005 | Islam et al. | |
| 2005/0158821 A1 | 7/2005 | Mello et al. | |
| 2007/0092558 A1 | 4/2007 | Heavner et al. | |
| 2009/0226969 A1 | 9/2009 | Johansson et al. | |
| 2009/0318963 A1 | 12/2009 | Asakura | |
| 2010/0113621 A1 | 5/2010 | Hayashi et al. | |
| 2011/0046686 A1 | 2/2011 | Kaplan et al. | |
| 2011/0136669 A1 | 6/2011 | Liebmann et al. | |
| 2012/0329992 A1 | 12/2012 | Johansson et al. | |
| 2013/0172478 A1 | 7/2013 | Bausch | |
| 2014/0058066 A1 | 2/2014 | Sekiyama et al. | |
| 2014/0245923 A1 | 9/2014 | Sugahara et al. | |
| 2015/0141618 A1 | 5/2015 | Ishikawa et al. | |
| 2015/0151264 A1 | 6/2015 | Baseeth et al. | |
| 2015/0291673 A1 | 10/2015 | Sekiyama | |
| 2015/0329587 A1* | 11/2015 | Osawa | C07K 1/145 530/353 |
| 2015/0361144 A1* | 12/2015 | Osawa | A61K 8/64 514/773 |
| 2015/0374833 A1* | 12/2015 | Osawa | A61K 47/42 514/1.1 |
| 2015/0376247 A1* | 12/2015 | Osawa | A61K 8/42 424/401 |
| 2019/0225646 A1* | 7/2019 | Homma | D01F 6/68 |

FOREIGN PATENT DOCUMENTS

| | | |
|---|---|---|
| CN | 1952225 | 4/2007 |
| CN | 101139501 | 3/2008 |
| CN | 101564914 | 10/2009 |
| CN | 101705559 | 5/2010 |
| CN | 101721739 | 6/2010 |
| CN | 101724920 | 6/2010 |
| CN | 102181948 | 9/2011 |
| CN | 103126974 | 6/2013 |
| CN | 103184570 | 7/2013 |
| CN | 103827139 | 5/2014 |
| CN | 104428124 | 3/2015 |
| EP | 0559725 | 9/1993 |
| EP | 0816505 | 1/1998 |
| EP | 1 038 908 | 9/2000 |
| EP | 2 774 934 | 9/2014 |
| EP | 2 940 032 | 11/2015 |
| EP | 2 990 414 | 3/2016 |
| JP | 02-240165 | 9/1990 |
| JP | 4-263614 | 9/1992 |
| JP | 5-263312 | 10/1993 |
| JP | 6-502993 | 4/1994 |
| JP | 8-74123 | 3/1996 |
| JP | 11-217506 | 8/1999 |
| JP | 2004-503204 | 2/2004 |
| JP | 2005-515309 | 5/2005 |
| JP | 2006-257000 | 9/2006 |
| JP | 2007-303015 | 11/2007 |
| JP | 2009-521921 | 6/2009 |
| JP | 2010-024586 | 2/2010 |
| JP | 4945768 B | 6/2012 |
| JP | 2012-136795 | 7/2012 |
| JP | 5427322 B | 2/2014 |
| JP | 5584932 | 9/2014 |
| WO | 92/09695 | 6/1992 |
| WO | 2001/036531 | 5/2001 |
| WO | 01/53333 | 7/2001 |
| WO | 01/070973 | 9/2001 |
| WO | 2007/078239 | 7/2007 |
| WO | WO 2008/004356 | 1/2008 |
| WO | 2010/015419 | 2/2010 |
| WO | 2010/123450 | 10/2010 |
| WO | 2011/113592 | 9/2011 |
| WO | 2012/165477 | 12/2012 |
| WO | 2013/065650 | 5/2013 |
| WO | 2013/065651 | 5/2013 |
| WO | 2014/103846 | 7/2014 |

OTHER PUBLICATIONS

Sashina, et al., "Structure and Solubility of Natural Silk Fibroiin", Russian Journal of Applied Chemistry, vol. 79, No. 6, Jun. 1, 2006, pp. 869-876.

Hardy, et al., "Polymeric Materials based on silk proteins", Polymer, vol. 49, No. 20, Sep. 23, 2008, pp. 4309-4327.

Lazaris, et al., "Spider Silk Fibers Spun from Soluble Recombinant Silk Produced in Mammalian Cells", Science, vol. 295, No. 5554, Jan. 18, 2002, pp. 472-476.

Extended European Search report issued in European Application No. 16776502.3, dated Jul. 26, 2018, 12 pages.

Extended European Search report issued in European Application No. 16776503.1, dated Jul. 20, 2018, 8 pages.

Teramoto, et al., "Chemical Modification of Silk Sericin in Lithium Chloride/Dimethyl Sulfoxide Solvent with 4-Cyanophenyl Isocyanate Biomacromolecules", 2004, 5(4), pp. 1392-1398.

Desai, et al., "Assessing the Structural Integrity of a Lyophilized Protein in Organic Solvents", Journal of the American Chemical Society, 1995, 117(14), pp. 3940-3945.

Waybright, et al., Overcoming Problems of Compound Storage in DMSO: Solvent and Process Alternatives, Journal of Biomolecular Screening, 2009, 14(6), pp. 708-715.

Sekiyama: "Artificial Synthesis of Dream Fiber "Spider Silk""; the Journal of the Japanese Society for Cutaneous Health, Aug. 2011, No. 66, pp. 1-10 with its partial English translation (13 pages).

(56) References Cited

OTHER PUBLICATIONS

Sugihara et al.: "Artificial Production of Spider Silk Fibers"; Polymer Preprints, Japan, 2011, vol. 60, No. 22, pp. 5338-5339 with its partial English translation (6 pages).

Teule et al.: "A protocol for the production of recombinant spider silk-like proteins for artificial fiber spinning"; Nature Protocols, 2009, vol. 4, No. 3, pp. 341-355.

Heim et al.: "Spider Silk: From Soluble Protein to Extraordinary Fiber", Angewandte. Chem. Int. Ed., 2009, vol. 48, No. 20, pp. 3584-3596.

Diao, et al., "Solubility and Electrospun Regenerated Fiber of Two Different Kinds of Spider Silk", Journal of Materials Science & Engineering, vol. 26, No. 6, Dec. 2008, pp. 918-922 with an English abstract.

Kearns, et al., "Silk-based Biomaterials for Tissue Engineering", Topics in Tissue Engineering, vol. 4, 2008, pp. 1-19.

Elices et al.: "Bioinspired Fibers Follow the Track of Natural Spider Silk"; Macromolecules (2011), 44, pp. 1166-1176.

Guerette et al.: "Silk Properties Determined by Gland-Specific Expression of a Spider Fibroin Gene Family"; Science (1996), vol. 727, pp. 112-115.

Xia et al.: "Native-sized recombinant spider silk protein produced in metabolically engineered *Escherichia coli* results in a strong fiber"; Proc. Natl. Acad. Sci. (PNAS) (2010), vol. 107, No. 32, pp. 14059-14063.

Agnarsson et al.: "Bioprospecting Finds the Toughest Biological Material: Extraordinary Silk from a Giant Riverine Orb Spider"; PLOS ONE, vol. 5, Issue 9, Sep. 2010.

Extended European Search Report, dated Feb. 9, 2015; European Application No. 12793074.1 (9 pages).

Office Action issued in corresponding Chinese Application No. 201380034158.4, dated Jul. 27, 2015, 7 pages.

Extended European Search Report issued in corresponding European Application No. 13810001.1, dated Dec. 18, 2015, 7 pages.

Office Action issued in corresponding Chinese Patent Application No. 201380034158.4, dated Feb. 29, 2016, 12 pages with a partial English translation.

Tsukada, et al., Structural Changes and Dyeability of Silk Fibroin Fiber Following Shrinkage in Neutral Salt Solution, J. Appl. Polymer Sci, 1994, 51(4), pp. 619-624.

Phipps, et al., "Analysis of Azo Dyes Using a Core Enhanced Technology Accucore HPLC Column", Thremo Scientific, Aug. 2011, pp. 1-2, Retrieved from <https://tools.thermofisher.com/content/sfs/brochures/ANCCSCENTAZODYE_0611.pdf>.

Lopez-Cortes, et al., "Screening and Isolation of PHB-Producing Bacteria in a Polluted Marine Microbial Mat", Microb Ecol (2008) 56:112-120, DOI 10.1007/s00248-007-9329-8.

Davies, et al., (2003) "Measurement of Isoketal Protein Adducts by Liquid Chromatography-electrospray Ionization/Tandem Mass Spectrometry", In Hensley & Ford (Eds.), Methods in Bioligial Oxidate Stress (Chapter 15, p. 30), Totowa, new Jersey Humana Ptress.

Office Action issued in corresponding Chinese Patent Application No. 201680020745.1, dated Aug. 5, 2020, 25 pages with translation.

\* cited by examiner

POLAR SOLVENT SOLUTION AND PRODUCTION METHOD THEREOF

TECHNICAL FIELD

The present invention relates to a polar solvent solution in which a solute containing a polyamino acid is dissolved in a polar solvent and production methods thereof.

BACKGROUND ART

Polar solvents such as dimethylsulfoxide (DMSO) can dissolve substances such as polymers easily, so they are used for acrylic fiber polymerization and acrylic fiber spinning solutions, or as solvents for polyimide polymerization, etc. The inventors of the present invention have proposed application of the polar solvents as solvents of polypeptides such as spider silk proteins and silk proteins in Patent Documents 1 and 2. Further, the inventors of the present invention also suggest adding inorganic salts to the polar solvents to increase the solubility of polypeptides in Patent Documents 1 and 2.

PRIOR ART DOCUMENTS

Patent Documents

Patent Document 1: JP 5427322 B
Patent Document 2. JP 5584932 B

DISCLOSURE OF INVENTION

Problem to be Solved by the invention

However, polar solvent solutions (e.g., solutions in which polypeptides such as spider silk proteins and silk proteins are dissolved in dimethylsulfoxide (DMSO)) may have reduced viscosities depending on how they are handled. The polar solvent solutions still have room for improvement in terms of performing stable spinning and casting when used as dopes for spinning, film, etc.

The present invention provides a polar solvent solution that enables stable spinning and casting when used as dopes for spinning, film, etc., and methods for producing the same.

Means for Solving Problem

The present invention relates to a polar solvent solution in which a solute containing a polyamino acid is dissolved in a polar solvent. The solution contains an inorganic salt, and a mole ratio of moisture to the inorganic salt (moisture/inorganic salt) in the solution is 2.5×m×n or less, where m represents the number of cations forming the inorganic salt and n represents a charge number of the cation.

The present invention also relates to a method for producing a polar solvent solution in which a solute containing a polyamino acid is dissolved in a polar solvent. The method includes: adding an inorganic salt to the solution and changing at least one of a moisture content and a content of the inorganic salt in the solution to adjust a viscosity of the solution.

The present invention also relates to a method for producing a polar solvent solution in which a solute containing a polyamino acid is dissolved in a polar solvent. The method includes: adding an inorganic salt to the solution and reducing a moisture content in the solution to increase a viscosity of the solution.

Effect of the Invention

In the polar solvent solution of the present invention in which the solute containing a polyamino acid and the inorganic salt are dissolved in the polar solvent, a mole ratio of moisture to the inorganic salt (moisture/inorganic salt) is 2.5×m×n or less. By doing so, the viscosity of the solution can be easily adjusted to a desired value, and spinning and casting are stabilized when the solution is used as dopes for spinning, film, etc. The production method of the present invention includes: adding an inorganic salt to the polar solvent solution and changing at least one of a moisture content and a content of the inorganic salt in the solution in which a solute containing a polyamino acid and the inorganic salt are dissolved in a polar solvent, so as to adjust a viscosity of the solution. By doing so, it is possible to obtain a polar solvent solution that enables stable spinning and casting.

DESCRIPTION OF THE INVENTION

Figure 1:
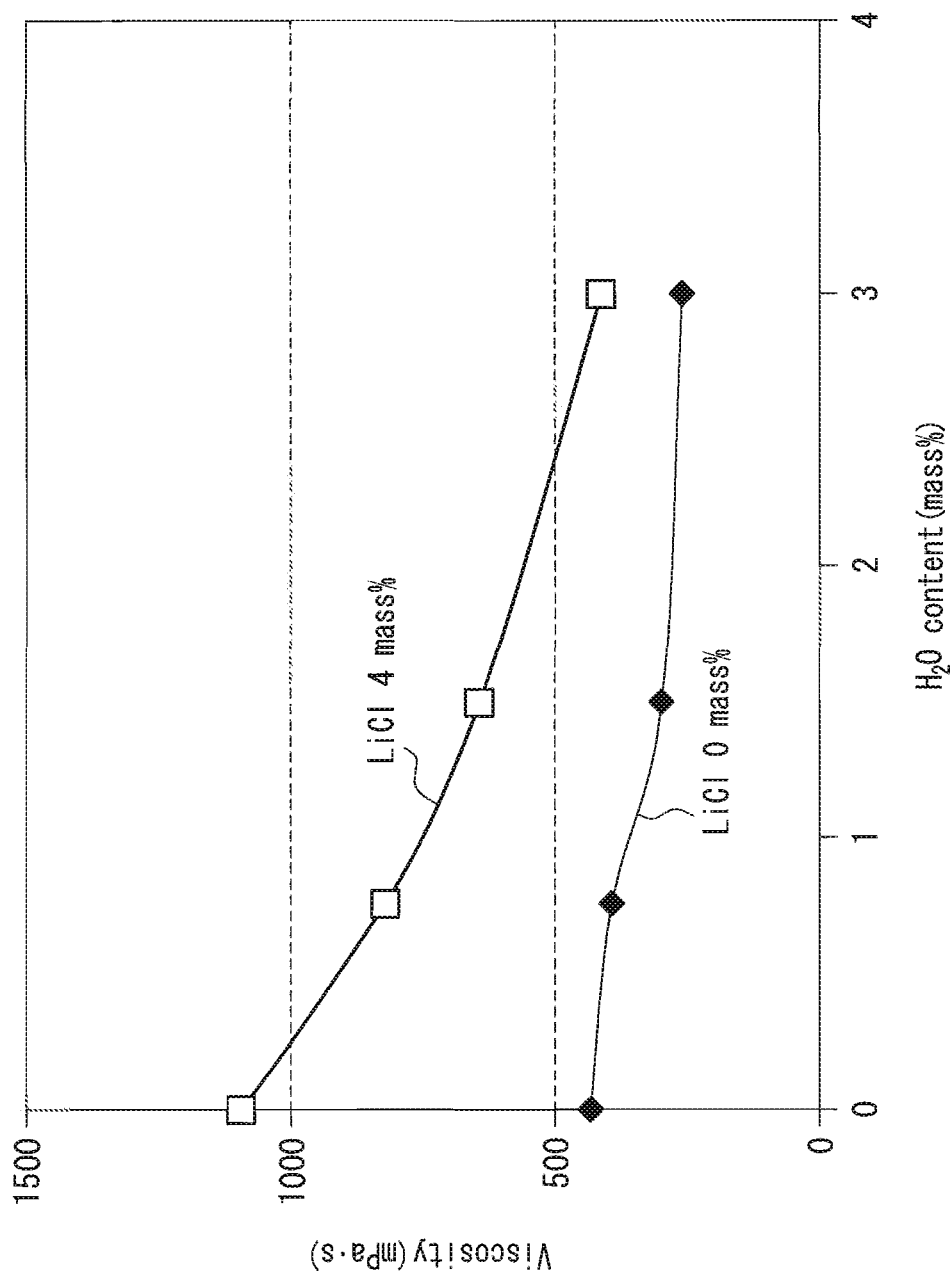
FIG. 1 is a graph showing a relationship between the addition amounts of moisture and LiCl and the viscosity of dopes in several examples and comparative examples of the present invention.

The inventors of the present invention found that polyamino acid (particularly polypeptide) itself, as well as a polar solvent solution in which a solute containing the polyamino acid is dissolved in polar solvent, readily absorbs moisture and lowers its viscosity. The inventors of the present invention also found that addition of an inorganic salt to the polar solvent solution can increase the solubility of the polyamino acid (polypeptide) and keep the viscosity of the solution high even when the solution absorbs a certain amount of moisture, and that lowering of the moisture content in the solution can keep the viscosity of the solution high even when the content of the inorganic salt in the solutions is low. From these findings, the inventors of the present invention arrived at an idea, to stabilize the viscosity of the solution at a desired value, of reducing the moisture content in the polar solvent solution, including moisture to be mixed into the solution due to the polyamino acid (particularly polypeptide) in the solute, and increasing or decreasing the content of the inorganic salt to control a ratio of the moisture content to the content of the inorganic salt in the solution to a specific value.

The solution contains one or more kinds of inorganic salts (by addition). When the solution contains plural kinds of inorganic salts, the mole ratio of the moisture to the inorganic salt (moisture/inorganic salt) in the solution is calculated using the total molar number of the plural kinds of inorganic salts contained in the solution. In other words, when the solution contains plural kinds of inorganic salts (by addition), the contents of the respective inorganic salts in the solution are adjusted so that the mole ratio of the moisture to the inorganic salt (moisture/inorganic salt) in the solution satisfies 2.5×m×n or less. In the present specification, the polar solvent solution is also called a dope. The following mainly describes a case of using polypeptide, which is an exemplary polyamino acid.

The mole ratio of the moisture to the inorganic salt (moisture/inorganic salt) in the solution is preferably 2.0× m×n or less (hereinafter, referred to as "Formula 1").

By doing so, the variation amount of the viscosity of the solution in accordance with the change in the content of the inorganic salt or the moisture content in the solution becomes large. Thus, the viscosity of the solution can be easily adjusted to a desired value simply by changing the content of the inorganic salt or the moisture content in the solution. In Formula 1 above, the number of cations forming the inorganic salt represented by m is preferably 1, and a charge number of the cation represented by n is preferably 1 or 2. By doing so, the viscosity of the solution can be adjusted to a desired value more easily and more reliably In order to decrease the mole ratio of the moisture to the inorganic salt in the solution, it is desirable to lower the moisture content in the solution. By doing so, the amount of the inorganic salt to be used can be reduced. Therefore, in the production method of the polar solvent solution of the present invention, it is preferred that the viscosity of the solution is increased by adding an inorganic salt to the solution while reducing the moisture content in the solution. Thereby, the viscosity of the solution is adjusted to a desired value while reducing the content of the inorganic salt in the solution. As a result, spinning and casting are stabilized when the solution is used as dopes for spinning, film, etc., while effectively avoiding an increase of the cost due to excess use of the inorganic salt.

In the production method of the present invention, by changing at least one of the moisture content and the content of the inorganic salt in the solution, or by reducing only the moisture content in the solution, the mole ratio of the moisture to the inorganic salt (moisture/inorganic salt) in the solution is controlled at preferably 2.5×m×n or less, more preferably 2.0×m×n or less. Thus, the viscosity of the solution can be adjusted to a desired value more reliably while reducing the amount of the inorganic salt to be added. As a result, a further cost reduction can be achieved.

In the production methods of the present invention, the adjustment for reducing the moisture content of the solution is achieved by, e.g., subjecting the solute or the solvent to heat drying or vacuum drying in advance, or adjusting the relative humidity of the atmosphere in at least one of the production and the storage of the solution, or vaporizing moisture of the produced solution by heating, or absorbing moisture using various kinds of moisture absorbents (moisture absorbent materials) such as zeolite, or combining these operations appropriately. Among the adjustment methods for reducing the moisture content of the solution described above, the method of drying the solute before dissolution in the solvent is favorably adopted. By doing so, the moisture content of the solution can be reduced more reliably and more efficiently. Moreover; in the case of changing the moisture content of the solution by adjusting the relative humidity of the atmosphere, it is advantageous that the relative humidity of the atmosphere in at least one of the production and the storage of the solution is kept at 1.3% RH or less. In order to keep the relative humidity of the atmosphere at 1.3% RH or less, it is preferred that processes such as the production and storage of the solution be carried out inside a dry room.

In the present invention, the moisture content of the polar solvent solution is preferably 0.6 mass % or more and 9.1 mass % or less, more preferably 0.6 mass % or more and 8.8 mass % or less, and further preferably 0.8 mass % or more and 8.8 mass % or less, based on 100 mass % of the solution. Within this range, the mole ratio of the moisture to the inorganic salt (moisture/inorganic salt) in the solution can be 2.5×m×n or less more reliably. Thus, the viscosity of the solution can be stably and reliably adjusted to a desired value simply by reducing the content of the inorganic salt in the solution, while advantageously providing the above-described characteristics to he exhibited by specifying the mole ratio.

It is preferred that the polar solvent that can be used in the present invention contain at least one aprotic polar solvent selected from the group consisting of (i) dimethylsulfoxide (DMSO), N,N-dimethylformamide (DMF), N,N-dimethylacetamide (DMA), and (iv) N-methyl-2-pyrrolidone (NMP). This is because these polar solvents can dissolve solutes containing polypeptides easily. Examples of the polar solvent that can be used in the present invention other than the solvents containing the above-described aprotic polar solvents include solvents containing protic polar solvents such as hexafluoroisopropanol (HFIP), formic acid, and various kinds of alcohols (e.g., lower alcohols having 1 to 6 carbon atoms such as methanol, ethanol, and 2-propanol). As the polar solvent, the ratio of the total amount of the at least polar solvent selected from the group consisting of (i)-(iv) described above is desirably 10 to 100 mass %, based on 100 mass % of the polar solvent as a whole. Within this range, the solubility of the solutes containing polypeptides can be enhanced.

Examples of the inorganic salt that can be used in the present invention include inorganic salts composed of Lewis acids and Lewis bases indicated below. Examples of the Lewis bases include oxo-acid ions (e.g., nitrate ions, perchlorate ions), metal oxo-acid ions (e.g., permanganate ions), halide ions, thiocyanate ions, and cyanate ions. Examples of the Lewis acids include metal ions such as alkali metal ions, alkaline-earth metal ions, polyatomic ions such as ammonium ions, and complex ions. Specific examples of the inorganic salt include: lithium salts such as lithium chloride, lithium bromide, lithium iodide, lithium nitrate, lithium perchlorate, and lithium thiocyanate; calcium salts such as calcium chloride, calcium bromide, calcium iodide, calcium nitrate, calcium perchlorate, and calcium thiocyanate; iron salts such as iron chloride, iron bromide, iron iodide, iron nitrate, iron perchlorate, and iron thiocyanate; aluminum salts such as aluminum chloride, aluminum bromide, aluminum iodide, aluminum nitrate, aluminum perchlorate, and aluminum thiocyanate; potassium salts such as potassium chloride, potassium bromide, potassium iodide, potassium nitrate, potassium perchlorate, and potassium thiocyanate; sodium salts such as sodium chloride, sodium bromide, sodium iodide, sodium nitrate, sodium perchlorate, and sodium thiocyanate; zinc salts such as zinc chloride, zinc bromide, zinc iodide, zinc nitrate, zinc perchlorate, and zinc thiocyanate; magnesium salts such as magnesium chloride, magnesium bromide, magnesium iodide, magnesium nitrate, magnesium perchlorate, and magnesium thiocyanate; barium salts such as barium chloride, barium bromide, barium iodide, barium nitrate, barium perchlorate, and barium thiocyanate; and strontium salts such as strontium chloride, strontium bromide, strontium iodide, strontium nitrate, strontium perchlorate, and strontium thiocyanate. Among these, in the present invention, the inorganic salt is preferably at least one selected from the group consisting of alkali metal halides, alkaline-earth metal halides, alkaline-earth metal nitrates, and thiocyanates. The alkali metal halides are, e.g., LiCl and LiBr, the alkaline-earth metal halides are, e.g., $CaCl_2$, etc., and the alkaline-earth metal nitrates are, e.g., $Ca(NO_3)_2$, etc., and thiocyanates are, e.g., NaSCN, etc. Among these, LiCl is preferred because it can keep the viscosity of the solution high.

The inorganic salt to be used in the present invention is used in an amount such that the mole ratio of the moisture to the inorganic salt (moisture/inorganic salt) in the solution would be 2.5×m×n or less, where m represents the number of cations forming the inorganic salt and n represents a charge number of the cation. Among the inorganic salts to be used in the present invention, an inorganic salt in which the number of cations is 1 and a charge number of the cation is 1 (e.g., LiCl, LiBr, NaSCN) needs to have the mole ratio of the moisture to the inorganic salt (moisture/inorganic salt) in the solution of 2.5 or less. Moreover, an inorganic salt in which the number of cations is 1 and a charge number of the cation is 2 (e.g., $CaCl_2$, $Ca(NO_3)_2$) needs to have the mole ratio of the moisture to the inorganic salt (moisture/inorganic salt) in the solution of 5.0 or less.

The inorganic salt to be used in the present invention is preferably contained in the solution in a ratio of 1 w/v % or more and 15 w/v % or less in total, based on 100 vol % of the solution. Thereby; the solutes containing polypeptides can be dissolved in the polar solvents more reliably. When the solution contains plural kinds of inorganic salts, the content of the plural kinds of inorganic salts in the solution is adjusted to be 1 w/v % or more and 15 w/v % or less in total. Note here that the "w/v (mass/vol)%" represents a percentage of the mass (g) of the inorganic salt(s) per unit volume (100 mL) of the solution.

Any solute that contains a polyamino acid (particularly polypeptide) can be used as the solute of the present invention. In the present specification, the polyamino acid refers to any polyamide compound polymerized through amide linkage between amino groups and carboxyl groups of amino acids. As the polyamino acid, the number of amino acids constituting the polyamide compound is preferably 15 or more, more preferably 20 or more, further preferably 30 or more, still further preferably 100 or more, and particularly preferably 500 or more, and preferably 6000 or less, more preferably 5000 or less, further preferably 3000 or less, and particularly preferably 2000 or less. The solute to be used in the present specification may be composed of, e.g., polyamine acid alone or contain one or more kinds of substances (e.g., carbonhydrate, synthetic resin) other than the polyamino acid in combination with the polypeptide. Moreover, the solute to be used in the present specification may be composed of, e.g., polypeptide alone or contain one or more kinds of substances (e.g., carbonhydrate, synthetic resin) other than the polypeptide in combination with the polypeptide. The polypeptide is preferably a structural protein, more preferably a structural protein including crystal regions. Such polypeptides can exhibit high strength and high toughness when formed into fibers, films, and the like. The structural protein refers to any protein involved in structures of living organisms, or any protein constituting structures created by living organisms. Examples of the structural protein include fibroin, sericin, collagen, keratin, elastin, and resillin.

The polypeptides are preferably fibroin such as spider silk proteins and silk proteins. Of these, spider silk proteins are particularly preferred because they have a high affinity for polar solvents and can be dissolved in the polar solvents easily.

When the polar solvent solution of the present invention is assumed to be 100 mass %, the concentration of the solute (e.g., spider silk protein) is desirably 2 to 50 mass %, further preferably 3 to 40 mass %, and particularly preferably 5 to 30 mass %. Within this range, the decrease or excessive increase of the viscosity of the polar solvent solution can be avoided effectively The polar solvent solution of the present invention, desirably in a state where undesired substances such as dust and bubbles have been removed, has a viscosity of preferably 10 to 100000 mPa·s, more preferably 15 to 20000 mPa·s, and further preferably 100 to 10000 mPa·s. The polar solvent solution within this viscosity range enables favorable wet spinning and film casting when used as dopes.

In the present invention, DMSO, which is suitably used as a polar solvent for dissolving a solute containing a polypeptide, is particularly advantageously used as, e.g., a solvent for dissolving a solute containing a spider silk protein. DMSO has a melting point of 18.4° C. and a boiling point of 189° C. DMSO has a much higher boiling point than hexafluoroisopropanol (HHP) and hexafluroacetone (HFAc) having boiling points of 59° C. and −26.5° C., respectively which have been used in conventional methods. Further, in view of the fact that DMSO has been used also in general industrial fields for acrylic fiber polymerization and acrylic fiber spinning solutions, and as solvents for polyimide polymerization, they are low cost substances with proven safety.

The spider silk proteins, which are exemplified as polypeptides to be contained in the solute of the present invention, are not limited particularly as long as they are natural spider silk proteins or proteins derived from or analogous to (hereinafter, simply referred to as "derived from") natural spider silk proteins. The proteins derived from natural spider silk proteins described herein are proteins having an amino acid sequence similar to or analogous to any of repetitive sequences of amino acids of natural spider silk proteins, examples of which includes variants, analogs, and derivatives of recombinant spider silk proteins and natural spider silk proteins. The spider silk proteins are preferably major dragline silk proteins produced in major ampullate glands of spiders or spider silk proteins derived therefrom, in terms of excellent tenacity. Examples of the major dragline silk proteins include major ampullate spidroins MaSp1 and MaSp2 derived from *Nephila clavipes*, and ADF3 and ADF4 derived from *Araneus cliadematus*, etc.

The spider silk proteins may be minor dragline silk proteins produced in minor ampullate glands of spiders or spider silk proteins derived therefrom. Examples of the minor dragline silk proteins include minor ampullate spidroins MiSp1 and MiSp2 derived from *Nephila clavipes*.

Other than these, the spider silk proteins may be flagelliform silk proteins produced in flagelliform glands of spiders or spider silk proteins derived therefrom. Examples of the flagelliform silk proteins include flagelliform silk proteins derived from *Nephila clavipes*, etc.

Examples of the spider silk proteins (polypeptides) derived from major dragline silk proteins include recombinant spider silk proteins containing two or more units of an amino acid sequence represented by the formula 1: REP1–REP2 (1), preferably recombinant spider silk proteins containing four or more units thereof, and more preferably recombinant spider silk proteins containing six or more units thereof. In the recombinant spider silk proteins, units of the amino acid sequence represented by the formula (1): REP1–REP2 (1) may be the same or different from each other.

In the formula (1), the REP1 represents a polyalanine region mainly constituted by alanine and expressed as (X1)p, and preferably the REP1 represents polyalanine. Here, p is not particularly limited, but preferably an integer of 2 to 20, more preferably an integer of 4 to 12. X1 represents alanine (Ala), serine (Ser), or glycine (Gly). The total number of alanine residues in the polyalanine region expressed as (X1)p is preferably 80% or more, more preferably 85% or more with respect to the total number of amino acid residues in the region. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 12 or less, and particularly preferably 10 or less. In the formula (1), the REP2 is an amino acid sequence composed of 10 to 200 amino acid residues. The total number of glycine, serine, glutamine, proline and alanine residues contained in the amino acid sequence is 40% or more, preferably 50% or more, and more preferably 60% or more with respect to the total number of amino acid residues contained therein.

In the major dragline silk, the REP1 corresponds to a crystal region in a fiber where a crystal β sheet is formed, and the REP2 corresponds to an amorphous region in a fiber where flexibility is high and most of the parts lack regular configurations. Further, the [REP1-REP2] corresponds to a repeating region (repetitive sequence) composed of the crystal region and the amorphous region, which is a characteristic sequence of dragline silk proteins.

Examples of the recombinant spider silk proteins containing two or more units of the amino acid sequence represented by the formula 1: REP1-REP2 (1) are recombinant spider silk proteins derived from ADF3 having an amino acid sequence represented by any of SEQ ID NO: 1, SEQ ID NO: 2 and SEQ ID NO: 3. The amino acid sequence represented by SEQ ID NO: 1 is an amino acid sequence obtained by the following mutation: in an amino acid sequence of ADF3 to the N-terminal of which has been added an amino acid sequence (SEQ ID NO: 4) composed of a start codon, His 10-tag and HRV3C Protease (Human rhinovirus 3C Protease) recognition site, $1^{st}$ to $13^{th}$ repetitive regions are about doubled and the translation ends at the $1154^{th}$ amino acid residue. The amino acid sequence represented by SEQ m NO: 2 is an amino acid sequence obtained by adding the amino acid sequence (SEQ ID NO: 4) composed of a start codon, His 10-tag and HRV3C Protease (Human rhinovirus 3C Protease) recognition site, to the N-terminal of a partial amino acid sequence of ADF3 (NCBI Genebank Accession No.: AAC47010, GI: 1263287) obtained from the NCBI database. The amino acid sequence represented by SEQ NO: 3 is an amino acid sequence obtained by the following mutation: in an amino acid sequence of ADF3 to the N-terminal of which has been added the amino acid sequence (SEQ ID NO: 4) composed of a start codon, His 10-tag and HRV3C Protease (Human rhinovirus 3C Protease) recognition site, $1^{st}$ to $13^{th}$ repetitive regions are about doubled. Further, the polypeptides containing two or more units of the amino acid sequence represented by the formula 1: REP1-REP2 (1) may be polypeptides that are composed of an amino acid sequence represented by any of SEQ NO: 1, SEQ NO: 2 and. SEQ ID NO: 3 in which one or more amino acids have been substituted, deleted, inserted and/or added and that have repeating regions composed of the crystal region and the amorphous region.

Examples of the spider silk proteins (polypeptides) derived from minor dragline silk proteins are recombinant spider silk proteins containing an amino acid sequence represented by the formula 2: REP3-REP4-REP5 (2). In the formula 2, the REP 3 indicates an amino acid sequence represented by (Gly-Gly-Z)s, the REP4 indicates an amino acid sequence represented by (Gly-Ala)l, and the REP5 indicates an amino acid sequence represented by (Ala)r. In the REP3, Z indicates any one of amino acids, particularly, it is preferably an amino acid selected from the group consisting of Ala, Tyr and Gln. Further, in the REP3, s is preferably 1 to 4. In the REP4, l is preferably 0 to 4. in the REP 5, r is preferably 1 to 6.

Among spider silks, the minor dragline silk is wound spirally from the center of a spider net, and used as a reinforcement of the net and a yarn to wrap a captured prey. The minor dragline silk is inferior to the major dragline silk in tensile strength, but is known to have high stretchability The reason for this is considered to be as follows: in the minor dragline silk, since many crystal regions are composed of regions where glycine and alanine are arranged alternately in succession, the hydrogen bonds of the crystal regions weaken easily as compared with the major dragline silk whose crystal regions are composed only of alanine.

Examples of the recombinant spider silk proteins (polypeptides) derived from flagelliform silk proteins include recombinant spider silk proteins containing an amino acid sequence represented by the formula 3: REP6 (3). In the formula 3, the REP 6 indicates an amino acid sequence represented by (U1)t or (U2)t. In the REP6, U1 indicates an amino acid sequence represented by Gly-Pro-Gly-X-X (SEQ ID NO: 12), and U2 indicates an amino acid sequence represented by Gly-Pro-Gly-Gly-X (SEQ ID NO: 13). In the U1 and U2, X indicates any one of amino acids, particularly, it is preferably an amino acid selected from the group consisting of Ala, Ser, Tyr, Gln, Val, Leu, and Ile, more preferably an amino acid selected from the group consisting of Ala, Ser, Tyr, Gln, and Vat A plurality of X may be the same or different from each other. In the REP6, t indicates a number of 4 or larger, preferably 10 or larger, and more preferably 20 or larger.

Among spider silks, the flagelliform silk does not have crystal regions but has repeating regions composed of the amorphous region, which is a major characteristic of the flagelliform silk. It is considered that since the major dragline silk and the like have repeating regions composed of the crystal region and the amorphous region, they have both high stress and stretchability. Meanwhile, regarding the flagelliform silk, the stress is inferior to that of the major dragline silk but the stretchability is high. The reason for this is considered to be that the flagelliform silk is composed mostly of the amorphous region.

The recombinant spider silk proteins (polypeptides) can be produced using a host that has been transformed by an expression vector containing a gene encoding a natural spider silk protein subjected to recombination. A method for producing a gene is not limited particularly, and it may be produced by amplifying a gene encoding a natural spider silk protein from a cell derived from spiders by a polymerase chain reaction (PCR) or the like, and cloning it, or may be synthesized chemically. A method for chemically synthesizing a gene also is not limited particularly, and it can be synthesized as follows, for example: based on information of amino acid sequences of natural spider silk proteins obtained from the NCBI web database or the like, oligonucleotides that have been synthesized automatically with AKTA oligopilot plus 10/100 (GE Healthcare Japan Corporation) are linked by PCR or the like. At this time, in order to facilitate purification and observation of protein, a gene may be synthesized that encodes a protein having the above-described amino acid sequence to the N-terminal of which has been added an amino acid sequence composed of a start codon and. His 10-tag. Examples of the expression vector include a plasmid, a phage, a virus and the like that can express protein based on a. DNA sequence. The plasmid-type expression vector is not limited particularly as long as it allows a target gene to be expressed in a host cell and it can amplify itself. For example, in the case of using *Escherichia coli.* Rosetta (DE3) as a host, a pET22b(+) plasmid vector, a pCold plasmid vector and the like can be used. Among these, in terms of productivity of protein, it is preferable to use the pET22b(+) plasmid vector. Examples of the host include animal cells, plant cells, microbes, etc.

EXAMPLES

Hereinafter, the present invention be described in further detail by way of examples. Note that the present invention is not limited to the following examples.
<Various Measurement Methods>
(1) Viscosity: The viscosities of polar solvent solutions (dopes) were measured using an EMS viscometer (EMS-01S) manufactured by Kyoto Electronics Manufacturing Co., Ltd.
(2) Relative humidity: The temperature and the dew-point temperature of an experiment environment were measured to calculate the relative humidity of the environment using a known calculation.
(3) Moisture percentage of dope: The moisture percentages of dopes were measured using a Hybrid Karl Fischer Moisture Titrator (MKH-700) manufactured by Kyoto Electronics Manufacturing Co., Ltd.
<Experiment 1>
1. Preparation of Spider Silk Proteins
<Gene Synthesis>
(1) Gene Synthesis of ADF3Kai.
A partial amino acid sequence of ADF3 (GI: 1263287), which is one of two principal dragline silk proteins of *Araneus diadematus,* was obtained from the NCBI web database, and synthesis of a gene encoding an amino acid sequence (SEQ ID NO: 2) was outsourced to GenScript, Inc. The amino acid sequence (SEQ ED NO: 2) is an amino acid sequence obtained by adding an amino acid sequence (SEQ ID NO: 4) composed of a start codon, His 10-tag and HRV3C Protease (Human rhinovirus 3C Protease) recognition site, to the N-terminal of said partial amino acid sequence of ADF3. As a result, a pUC57 vector to which a gene of ADF3Kai having a base sequence represented by SEQ ID NO: 5 had been introduced was obtained (having an Nde I site immediately upstream of 5' terminal of the gene and an Xba I site immediately downstream of 5' terminal thereof). Thereafter, the gene was subjected to a restriction enzyme treatment with Nde I and EcoR I, and recombined into a pET22b(+) expression vector.
(2) Gene Synthesis of ADF3Kai—Large
The half of the gene sequence of ADF3Kai on the 5' side (hereinafter, referred to as a sequence A) was amplified by the PCR reaction using ADF3Kai as a template, and a T7 promoter primer (SEQ ID NO: 8) and a Rep Xba I primer (SEQ ID NO: 9). The obtained DNA fragment of the sequence A was recombined into a pUC118 vector that had been subjected to the restriction enzyme treatment with Nde I and Xba I in advance using a Mighty Cloning Kit (manufactured by TAKARA BIO INC.). Similarly, the half of the gene sequence of ADF3Kai on the 3' side (hereinafter, referred to as a sequence B) was amplified by the PCR reaction using ADF3Kai as a template, and an Xba I Rep primer (SEQ ED NO: 10) and a T7 terminator primer (SEQ ID NO: 11). The obtained DNA fragment of the sequence B was recombined into a pUC118 vector that had been subjected to the restriction enzyme treatment with Xba I and EcoR I in advance using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that had been subjected to the restriction enzyme treatment with. Nde I and EcoR I in advance were subjected to a ligation reaction and transformed into *Escherichia coli* DH5α. After confirmation of the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×l Genetic Analyzer (Applied Biosystems). Consequently, the construction of a gene of ADF3Kai——Large represented by SEQ ID NO: 6 was confirmed. The amino acid sequence of ADF3Kai—Large is as represented by SEQ ID NO: 3.
(3) Gene Synthesis of ADF3Kai—Large—NRSH1
With a pET22b(+) vector to which the gene of ADF3Kai—Large obtained above had been introduced used as a template, through site-directed mutagenesis using a PrimeSTAR Mutagenesis Basal Kit (manufactured by TAKARA BIO INC.), a codon GGC corresponding to the $1155^{th}$ amino acid residue, i.e., glycine (Gly), in the amino acid sequence of ADF3Kai—Large (SEQ ID NO: 3) was mutated into a stop codon TAA, and a gene of ADF3Kai—Large—NRSH1 represented by SEQ ID NO: 7 was constructed on the pET22b(+). The accuracy of the introduction of the mutation was checked by the sequence reaction using the 3130×l Genetic Analyzer (Applied Biosystems). The amino acid sequence of ADF3Kai—Large—NRSH1 is as represented by SEQ ID NO: 1.
<Expression of Protein>
The pET22b(+) expression vector containing the gene sequence of ADF3Kai—Large—NRSH1 was transformed into *Escherichia coli* Rosetta (DE3). The obtained single colony was incubated for 15 hours in 2 ml of an LB culture medium containing ampicillin. Thereafter, 1.4 ml of the culture solution was added to 140 ml of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2×YT culture medium containing ampicillin, together with 140 ml of 50% glucose, and incubated further to the $OD_{600}$ of 4.0. Thereafter, isopropyl-6-thiogalactopyranoside (IPTG) was added to the obtained culture solution with the $OD_{600}$ of 4.0 so that the final concentration would be 0.5 mM, thereby inducing the expression of protein. After a lapse of two hours from the addition of IPTG, the culture solution was centrifuged and bacterial cells were collected. Protein solutions prepared from the culture solution before the addition of IPTG and after the addition of IPTG were each electrophoresed in a polyacrylamide gel. Consequently, a target band size (about 101.1 kDa) was observed with the addition of IPTG, and the expression of the target protein was confirmed.

Purification (1) About 50 g of bacteria cells of the *Escherichia coli* expressing the ADF3Kai—Large—NRSH1 protein and 300 ml of a buffer solution AI (20 ml Tris-HCI, pH 7.4) were placed in a centrifuge tube (1000 ml). After dispersing the bacteria cells with a mixer ("T18 basic ULTRA TURRAX" manufactured by IKA, level 2), the dispersion was centrifuged (11,000 g, 10 minutes, room temperature) with a centrifuge ("Model 7000" manufactured by Kubota Corporation), and a supernatant was discarded.

(2) To a precipitate (bacteria cells) obtained by the centrifugation, 300 ml of the buffer solution Al and 3 ml of 0.1 M PMSF (dissolved by isopropanol) were added. After dispersing the precipitate for 3 minutes with the mixer (level 2) manufactured by IKA, the bacteria cells were disrupted repeatedly for three times using a high-pressure homogenizer ("Panda Plus 2000" manufactured by GEA Niro Soavi).

(3) To the disrupted bacterial cells, 300 ml of a buffer solution B (50 mM Tris-HCL, 100 mM NaCl, pH 7.0) containing 3 w/v % of SDS was added. After dispersing well the bacterial cells with the mixer (level 2) manufactured by IKA, the dispersion was stirred for 60 minutes with a shaker (manufactured by TAITEC CORPORATION, 200 rpm, 37° C.). Thereafter, the stirred dispersion was centrifuged (11,000 g, 30 minutes, room temperature) with the centrifuge manufactured by Kubota Corporation, and a supernatant was discarded, whereby SDS washing granules (precipitate) were obtained.

(4) The SDS washing granules were suspended in a DMSO solution containing 1M lithium chloride so that the concentration would be 100 mg/ml, and heat-treated for 1 hour at 80° C. Thereafter, the heated suspension was centrifuged (11,000 g, 30 minutes, room temperature) with the centrifuge manufactured by Kubota Corporation, and the supernatant was collected.

(5) Ethanol in an amount three times greater than that of the collected supernatant was prepared. The collected supernatant was added to the ethanol, and left to stand still for 1 hour at room temperature. Thereafter, the resultant was centrifuged (11,000 g, 30 minutes, room temperature) with the centrifuge manufactured by Kubota Corporation to collect aggregated protein. Next, a process of washing aggregated protein using pure water and a process of collecting aggregated protein by centrifugation were repeated three times, and then moisture was removed by a freeze dryer to collect freeze-dried powder. The purification degree of the target protein ADF3Kai—Large—NRSH1 (about 56.1 kDa) in the obtained freeze-dried powder was checked by analyzing images of the results of polyacrylamide gel electrophoresis (CBB staining) of said protein powder using Totallab (nonlinear dynamics Ltd.). As a result, the purification degree of ADF3Kai—Large—NRSH1 was about 85%.

2. Adjustment of Dope and Viscosity Measurement

The spider silk protein (powder) obtained above was subjected to vacuum drying (bone dry), and the spider silk protein in the absolute dry state was dissolved in four DMSO solvents of a predetermined amount prepared beforehand so that the concentration of the protein of the respective solvents would be 15 mass %. into the four DMSO solvents containing the spider silk protein, LiCl (inorganic salt) was dissolved at a concentration of 4.0 w/v % (mass/vol %) and different amounts of pure water were added as indicated in Table 1 below (however, in one of the four DMSO solvents, only LiCl was dissolved and no pure water was added), so as to prepare four kinds of dopes containing LiCl and having different moisture contents (added amounts) (Examples 1-4). Here, the LiCl concentration of 4.0 w/v % described herein means that 4 g of LiCl is contained in 100 mL of the solution. In addition to the dopes of Examples 1-4, the spider silk protein (powder) in the absolute dry state obtained above was dissolved in four DMSO solvents of a predetermined amount prepared beforehand so that the concentration of the protein of the respective solvents would be 15 mass %. To three of the four DMSO solvents containing the spider silk protein, different amounts of pure water only were added as indicated in Table 1 below so as to prepare three kinds of dopes not containing Cl and having different moisture contents (added amounts) (Comparative Examples 2-4) and one dope not containing moisture or LiCl (Comparative Example 1). In the preparation of the eight kinds of dopes of Examples 1-4 and Comparative Examples 1-4, the spider silk protein was dissolved in the DMSO solvents for 5 hours using a shaker, and then dust and bubbles were removed from the solvents. This process was all performed in a dry room at a relative humidity of 1.3% RH or less. The storage was also in a dry room at a relative humidity of 1.3% RH or less. The viscosities of the dopes of Examples 1-4 and the dopes of Comparative Examples 1-4 were measured at 25° C. Table 1 below and FIG. 1 show the results.

TABLE 1

|  | Moisture content in dope (mass %) | LiCl content (w/v %) | $H_2O$/LiCl mole ratio | Viscosity (mPa · s) |
|---|---|---|---|---|
| Ex. 1 | 0 | 4.0 | 0 | 1094 |
| Ex. 2 | 0.75 | 4.0 | 0.6 | 822 |
| Ex. 3 | 1.5 | 4.0 | 1.2 | 642 |
| Ex. 4 | 3.0 | 4.0 | 2.3 | 415 |
| Comp. Ex. 1 | 0 | 0 | — | 434 |
| Comp. Ex. 2 | 0.75 | 0 | — | 393 |
| Comp. Ex. 3 | 1.5 | 0 | — | 299 |
| Comp. Ex. 4 | 3.0 | 0 | — | 261 |

*Ex.: Example, Comp. Ex.: Comparative Example

As is clear from Table 1 and FIG. 1, as to the dopes of Examples 1-4 containing LiCl, the viscosity was high as the moisture content was low, i.e., the dope of Example 1 with a moisture content of 0 mass % had the highest viscosity. Also as to the dopes of Comparative Examples 1-4 not containing LiCl, the viscosity was high as the moisture content was low. However; when the dopes of Examples 1-4 are respectively compared with the dopes of Comparative Examples 1-4 having the same moisture content, the former had the higher viscosity than the latter, and the former showed equal or higher viscosity rise than the latter in accordance with a decrease in the moisture content. These results indicate that the viscosity can be increased by reducing the moisture content in the dope, and the viscosity can be maintained still higher by adding LiCl to the dope. It was also confirmed that spinning and casting can be stabilized with the dopes of Examples 1-4.

When the dope of Example 4 and that of Comparative Example 1 are compared, their viscosities are almost the same. This indicates that a dope with a moisture content of 0 and a LiCl content of 0 can have the same level of viscosity as a dope with a moisture content of 3.0 mass % and a LiCl content of 4.0 w/v %. From these results, it was confirmed that in the production of dopes having a desired viscosity, the amount of the inorganic salt to be added to the dopes can be reduced by reducing the moisture content in the dopes.

<Experiment 2>

Figure 2:
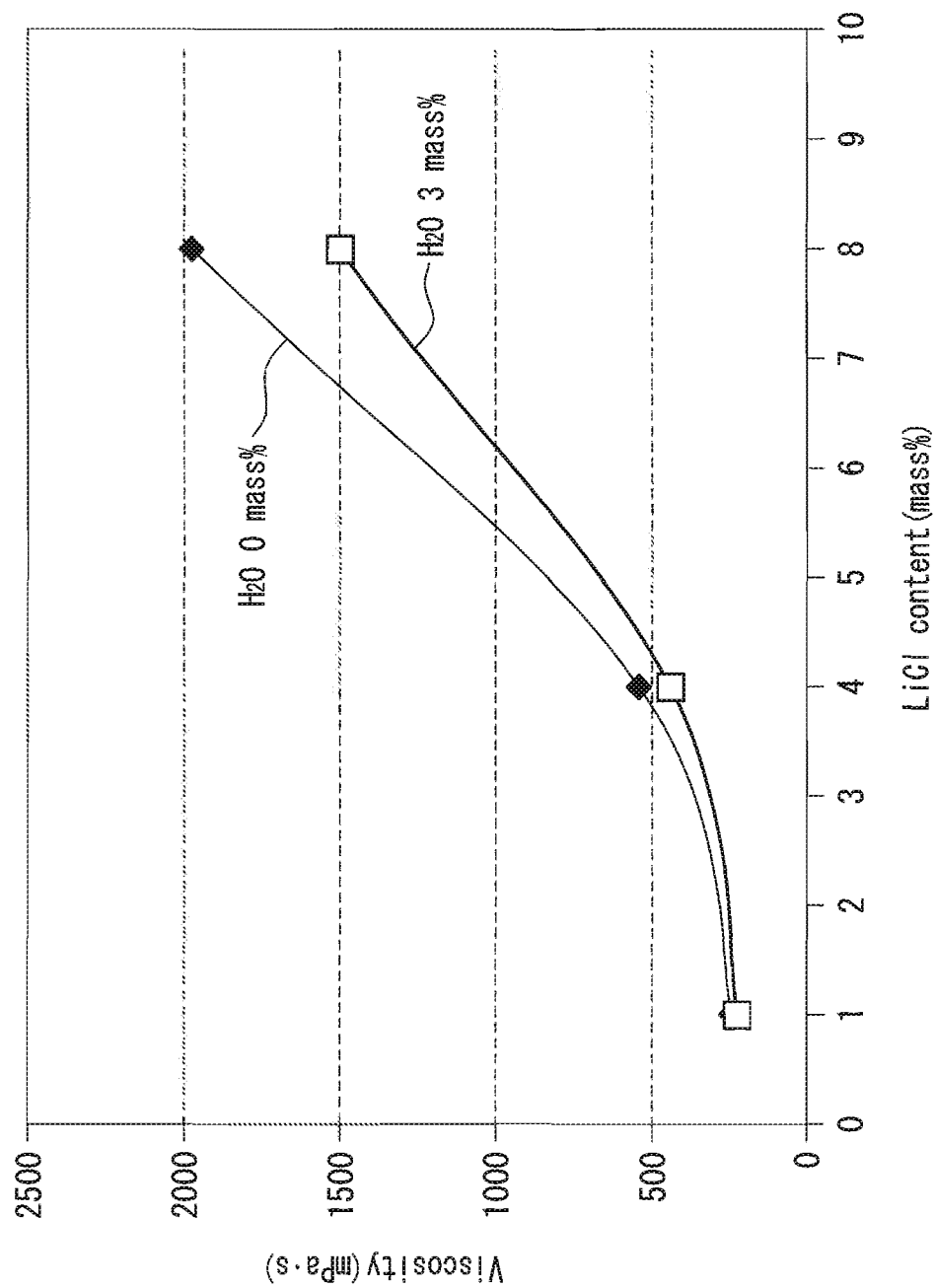
FIG. 2 is a graph showing a relationship between with or without moisture, the addition amount of LiCl, and the viscosity of dopes in several examples of the present invention.

This experiment was carried out to examine a relationship between with or without moisture, the LiCl content, and the viscosity: The spider silk protein (powder) in the absolute dry state obtained in the above-described manner was dissolved in three DMSO solvents of a predetermined amount prepared beforehand so that the concentration of the protein of the respective solvents would be 15 mass %. To the three DMSO solvents containing the spider silk protein, LiCl (inorganic salt) was added as indicated in Table 2 below to produce three kinds of dopes with a moisture content of 0 and having different LiCl contents (Examples 5-7). The three kinds of dopes (Examples 5-7) were produced in a dry room at a relative humidity of 1.3% RH or less, and they were stored also in a dry room at a relative humidity of 1.3% RH or less. In addition to the dopes of Examples 5-7, the spider silk protein (powder) in the absolute dry state obtained in the above-described manner was dissolved in three DMSO solvents of a predetermined amount prepared beforehand so that the concentration of the protein of the respective solvents would be 15 mass %. To the three DMSO solvents containing the spider silk protein, moisture and LiCl (inorganic salt) were added as indicated in Table 2 below to produce three kinds of dopes with a moisture content of 3 mass % and having different LiCl contents (Comparative Example 5, and Examples 8, 9). Thereafter, the viscosities of the six kinds of the dopes of Examples 5-9 and Comparative Example 5 were measured at 25° C. Table 2 below and FIG. 2 show the results.

TABLE 2

| | Moisture content in dope (mass %) | LiCl content (w/v %) | $H_2O$/LiCl mole ratio | Viscosity (mPa · s) |
|---|---|---|---|---|
| Ex. 5 | 0 | 1.0 | 0 | 241 |
| Ex. 6 | 0 | 4.0 | 0 | 544 |
| Ex. 7 | 0 | 8.0 | 0 | 1975 |
| Comp. Ex. 5 | 3.0 | 1.0 | 9.6 | 224 |
| Ex. 8 | 3.0 | 4.0 | 2.3 | 449 |
| Ex. 9 | 3.0 | 8.0 | 1.2 | 1517 |

*Ex.: Example, Comp. Ex.: Comparative Example

As is clear from Table 2 and FIG. 2, it was confirmed that the viscosities of the dopes can be increased by reducing the moisture content in the dopes, and dopes having a target viscosity can be obtained by adding a larger amount of LiCl even when moisture is mixed into the dopes. This clearly indicates that the viscosities of the dopes can be easily adjusted to desired values by changing the moisture content and/or the content of the inorganic salt in the dopes.

<Experiment 3>

Figure 3:
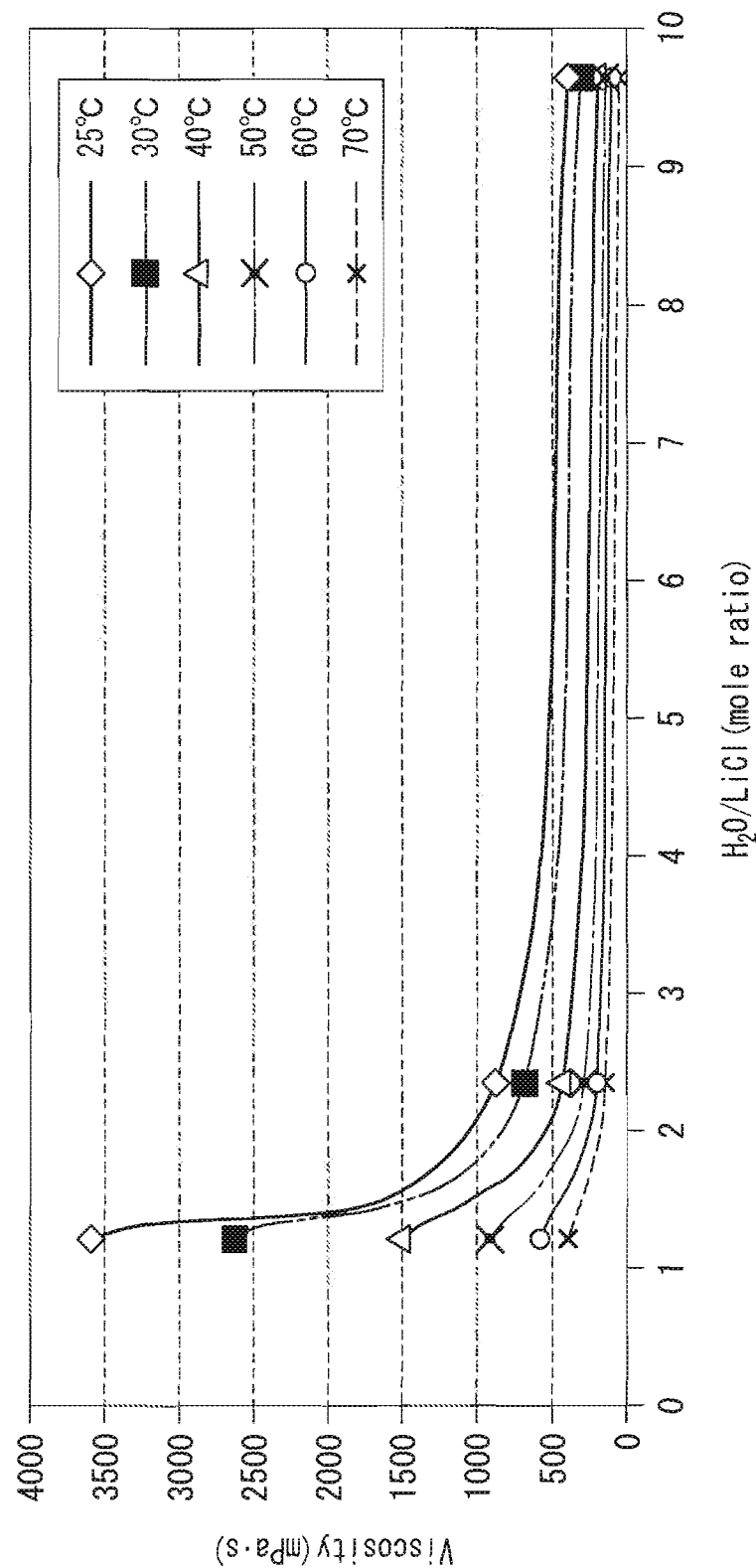
FIG. 3 is a graph showing a relationship between the mole ratio of $H_2O/CaCl_2$ and the viscosity of dopes depending on temperature in several examples of the present invention.

This experiment was carried out to examine a relationship between a mole ratio of $H_2O$/TiCl and the viscosity of dopes depending on temperature. Three kinds of dopes of Examples 8, 9 and Comparative Example 5 obtained in the above-described manner were used. The viscosities of the three kinds of the dopes at 25° C., 30° C., 40° C., 50° C., 60° C., and 70° C. were measured. FIG. 3 shows the results.

As is clear from FIG. 3, by controlling the mole ratio of $H_2O$/LiCl to be 2.5 or less, the variation amount of the viscosity in accordance with the change in the LiCl content or the change in the moisture content in the dope can be large, whereby the viscosity of the dope can be easily adjusted to a desired value simply by changing the LiCl content and/or the moisture content in the dope.

<Experiment 4>

Figure 4:
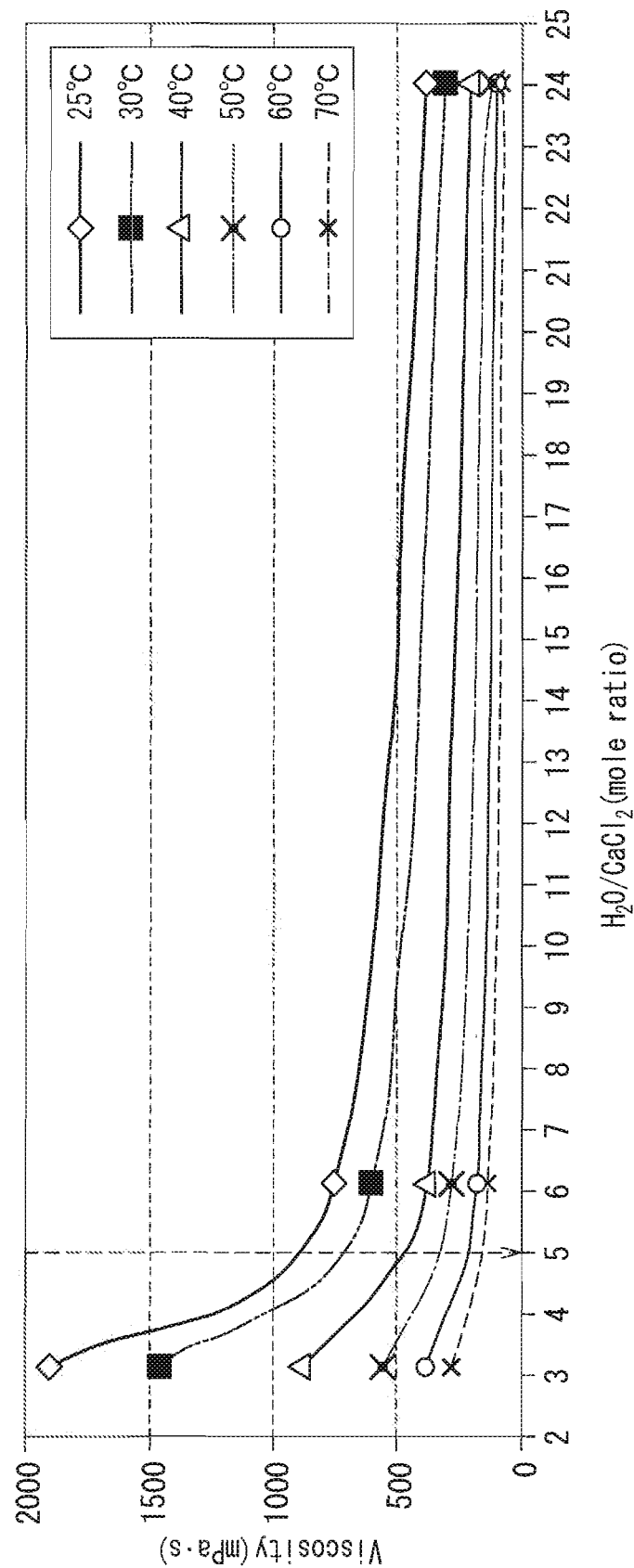
FIG. 4 is a graph showing a relationship between the mole ratio of $H_2O/CaCl_2$ and the viscosity of dopes depending on temperature in several examples of the present invention.

This experiment was carried out to examine a relationship between a mole ratio of $H_2O$/$CaCl_2$ and the viscosity of dopes depending on temperature. Three kinds of dopes of Example 10 and Comparative Examples 6, 7 were produced in the same manner as in the production of the three kinds of dopes of Examples 8, 9 and Comparative Example 5 except that $CaCl_2$ was used instead of LiCl as the inorganic salt. The viscosity of the dope containing 3.0 mass % of moisture and 1.0 w/v % of $CaCl_2$ (Comparative Example 6), the viscosity of the dope containing 3.0 mass % of moisture and 4.0 w/v % of $CaCl_2$ (Comparative Example 7), and the viscosity of the dope containing 3.0 mass % of moisture and 8.0 w/v % of $CaCl_2$ (Example 10) were measured at 25° C., 30° C., 40° C., 50° C., 60° C., and 70° C., respectively FIG. 4 shows the results. Table 3 below shows the mole ratios of $H_2O$/$CaCl_2$ of the dopes of the Comparative Examples 6, 7 and Example 10.

TABLE 3

| | Moisture content in dope (mass %) | $CaCl_2$ content (w/v %) | $H_2O$/$CaCl_2$ mole ratio |
|---|---|---|---|
| Comp. Ex. 6 | 3.0 | 1.0 | 24.1 |
| Comp. Ex. 7 | 3.0 | 4.0 | 6.1 |
| Ex. 10 | 3.0 | 8.0 | 3.2 |

*Ex.: Example, Comp. Ex.: Comparative Example

As is clear from FIG. 4, by controlling the mole ratio of $H_2O$/$CaCl_2$ to be 5.0 or less, the variation amount of the viscosity in accordance with the change in the $CaCl_2$ content or the change in the moisture content in the dope can be large, whereby the viscosity of the dope can be easily adjusted to a desired value simply by changing the $CaCl_2$ content and/or the moisture content in the dope.

INDUSTRIAL APPLICABILITY

The polar solvent solution of the present invention is useful for wet spinning, film casting, gels, particles, mesh materials, and various types of moldings.

Sequence Listing Free Text
   SEQ ID NOS: 1-4, 12, 13 amino acid sequences
   SEQ ID NOS: 5-7 base sequences
   SEQ ID NOS: 8-11 primer sequences

The invention claimed is:

1. A polar solvent solution comprising:
a solute containing a polyamino acid;
a polar solvent; and
an inorganic salt,
wherein the solute containing a polyamino acid is dissolved in the polar solvent, and the inorganic salt is added to the solution,
a mole ratio of moisture to the inorganic salt in the solution is 2.5×m×n or less, where m represents the number of cations forming the inorganic salt and n represents a charge number of the cation, and
at least one of a moisture content and a content of the inorganic salt in the solution is chosen to provide a desired viscosity for the solution, and the viscosity of the solution is 100 to 10000 mPa·s.

2. The polar solvent solution according to claim 1, wherein the polyamino acid is a polypeptide.

3. The polar solvent solution according to claim 2, wherein the polypeptide is a structural protein.

4. The polar solvent solution according to claim 3, wherein the structural protein includes a crystal region.

5. The polar solvent solution according to claim 2, wherein the polypeptide is a spider silk protein.

6. The polar solvent solution according to claim 1, wherein the solution has a moisture content of 0.6% by mass or more and 9.1% by mass or less based on 100% by mass of the solution.

7. The polar solvent solution according to claim 1, wherein the polar solvent contains at least one selected from the group consisting of dimethylsulfoxide (DMSO), N,N-dimethylformamide (DMF), N,N-dimethylacetamide (DMA), and N-methyl-2-pyrrolidone (NMP).

8. The polar solvent solution according to claim 1, wherein the inorganic salt is at least one selected from alkali metal halides, alkaline-earth metal halides, alkaline-earth metal nitrates, and thiocyanates.

9. The polar solvent solution according to claim 1, wherein the solution has a content of the inorganic salt of 1 w/v% or more and 15 w/v% or less based on 100% by volume of the solution.

* * * * *

SEQUENCE LISTING

<160> NUMBER OF SEQ ID NOS: 13

<210> SEQ ID NO 1
<211> LENGTH: 1154
<212> TYPE: PRT
<213> ORGANISM: Artificial
<220> FEATURE:
<223> OTHER INFORMATION: ADF3Kai-Large-NRSH1

<400> SEQUENCE: 1

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gln Gln Gly Pro Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
        210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gly Pro Gly Gln Gly Pro Gly Gly
            420             425             430

Gln Gly Ala Tyr Gly Pro Gly Ala Ser Ala Ala Gly Ala Ala Gly
        435             440             445

Gly Tyr Gly Pro Gly Ser Gly Gln Gln Gly Pro Gly Gln Gln Gly Pro
    450             455             460

Gly Gln Gln Gly Pro Gly Gln Gln Gly Pro Gly Gln Gln Gly Pro Gly
465             470             475             480

Gln Gln Gly Pro Gly Gln Gln Gly Pro Gly Gln Gln Gly Pro Tyr Gly
            485             490             495

Pro Gly Ala Ser Ala Ala Ala Ala Ala Gly Gly Tyr Gly Pro Gly
        500             505             510

Ser Gly Gln Gln Gly Pro Gly Gln Gln Gly Pro Gly Gln Gln Gly Pro
    515             520             525

Gly Gly Gln Gly Pro Tyr Gly Pro Gly Ala Ala Ser Ala Ala Val Ser
    530             535             540

Val Ser Arg Ala Arg Ala Gly Ser Gly Gln Gln Gly Pro Gly Gln Gln
545             550             555             560

Gly Pro Gly Gln Gln Gly Pro Gly Gln Gln Gly Pro Tyr Gly Pro Gly
            565             570             575

Ala Ser Ala Ala Ala Ala Ala Ala Gly Gly Tyr Gly Pro Gly Ser Gly
        580             585             590

Gln Gln Gly Pro Ser Gln Gly Pro Gly Gln Gln Gly Pro Gly Gly
            595             600             605

Gln Gly Pro Tyr Gly Pro Gly Ala Ser Ala Ala Ala Ala Ala Gly
    610             615             620

Gly Tyr Gly Pro Gly Ser Gly Gln Gln Gly Pro Gly Gln Gln Gly Pro
625             630             635             640

Tyr Gly Pro Gly Ser Ser Ala Ala Ala Ala Ala Gly Gly Asn Gly
            645             650             655

Pro Gly Ser Gly Gln Gln Gly Ala Gly Gln Gln Gly Pro Gly Gln Gln
        660             665             670

Gly Pro Gly Ala Ser Ala Ala Ala Ala Ala Gly Gly Tyr Gly Pro
    675             680             685

Gly Ser Gly Gln Gln Gly Pro Gly Gln Gln Gly Pro Gly Gly Gln Gly
    690             695             700

Pro Tyr Gly Pro Gly Ala Ser Ala Ala Ala Ala Ala Gly Gly Tyr
705             710             715             720

Gly Pro Gly Ser Gly Gln Gly Pro Gly Gln Gln Gly Pro Gly Gly Gln
            725             730             735

Gly Pro Tyr Gly Pro Gly Ala Ser Ala Ala Ala Ala Ala Gly Gly
        740             745             750

Tyr Gly Pro Gly Ser Gln Gln Gly Pro Gly Gln Gln Gly Pro Gly
    755             760             765

Gln Gln Gly Pro Gly Gly Gln Gly Pro Tyr Gly Pro Gly Ala Ser Ala
    770             775             780

Ala Ala Ala Ala Gly Gly Tyr Gly Pro Gly Tyr Gly Gln Gln Gly
785             790             795             800

Pro Gly Gln Gln Gly Pro Gly Gln Gly Pro Tyr Gly Pro Gly Ala
            805             810             815

Ser Ala Ala Ser Ala Ala Ser Gly Gly Tyr Gly Pro Gly Ser Gly Gln
        820             825             830

```
Gln Gly Pro Gly Gln Gly Pro Gly Gln Gly Pro Tyr Gly Pro
            835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro
865                 870                 875                 880

Gln Gln Gly Pro Gly Gly Gln Gly Pro Tyr Gly Pro Gly Ala Ser
                885                 890                 895

Ala Ala Ala Ala Ala Gly Gly Tyr Gly Pro Gly Ser Gly Gln Gln
            900                 905                 910

Pro Gly Gln Gln Gly Pro Gly Gln Gln Gly Pro Gly Gln Gln Gly Pro
        915                 920                 925

Gly Gln Gln Gly Pro Gly Gln Gln Gly Pro Gly Gln Gln Gly Pro Gly
    930                 935                 940

Gln Gln Gly Pro Gly Gln Gln Gly Pro Gly Gly Gly Ala Tyr Gly
945                 950                 955                 960

Pro Gly Ala Ser Ala Ala Ala Gly Ala Ala Gly Tyr Gly Pro Gly
                965                 970                 975

Ser Gly Gln Gln Gly Pro Gly Gln Gln Gly Pro Gly Gln Gln Gly Pro
        980                 985                 990

Gly Gln Gln Gly Pro Gly Gln Gln Gly Pro Gly Gln Gln Gly Pro Gly
    995                 1000                1005

Gln Gln Gly Pro Gly Gln Gln Gly Pro Tyr Gly Pro Gly Ala Ser
    1010                1015                1020

Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 2
<211> LENGTH: 660
<212> TYPE: PRT
<213> ORGANISM: Artificial
<220> FEATURE:
<223> OTHER INFORMATION: ADF3Kai

<400> SEQUENCE: 2

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30
```

```
Gly Pro Gly Gln Gly Pro Gly Gln Gly Pro Gly Gln Gly
        35                  40                  45
Pro Tyr Gly Pro Gly Ala Ser Ala Ala Ala Ala Gly Gly Tyr
    50                  55                  60
Gly Pro Gly Ser Gly Gln Gln Gly Pro Ser Gln Gly Pro Gly Gln
65                  70                  75                  80
Gln Gly Pro Gly Gly Gln Gly Pro Tyr Gly Pro Gly Ala Ser Ala Ala
                85                  90                  95
Ala Ala Ala Ala Gly Gly Tyr Gly Pro Gly Ser Gly Gln Gln Gly Pro
                100                 105                 110
Gly Gly Gln Gly Pro Tyr Gly Pro Gly Ser Ser Ala Ala Ala Ala Ala
            115                 120                 125
Ala Gly Gly Asn Gly Pro Gly Ser Gly Gln Gln Gly Ala Gly Gln Gln
            130                 135                 140
Gly Pro Gly Gln Gln Gly Pro Gly Ala Ser Ala Ala Ala Ala Ala Ala
145                 150                 155                 160
Gly Gly Tyr Gly Pro Gly Ser Gly Gln Gln Gly Pro Gly Gln Gln Gly
                165                 170                 175
Pro Gly Gly Gln Gly Pro Tyr Gly Pro Gly Ala Ser Ala Ala Ala Ala
            180                 185                 190
Ala Ala Gly Gly Tyr Gly Pro Gly Ser Gly Gln Gly Pro Gly Gln Gln
            195                 200                 205
Gly Pro Gly Gly Gln Gly Pro Tyr Gly Pro Gly Ala Ser Ala Ala Ala
210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
                245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gly Gln Gly Pro
    275                 280                 285
Tyr Gly Pro Gly Ala Ser Ala Ala Ser Ala Ala Ser Gly Gly Tyr Gly
    290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
        325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Gly Tyr Gly Pro Gly
        370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
            435                 440                 445
```

Gly Tyr Gly Pro Gly Ser Gly Gln Gln Gly Pro Gln Gln Gly Pro
            450                 455                 460
Gly Gln Gly Pro Gly Gln Gly Pro Gly Gln Gln Gly Pro Gly Gln
465                 470                 475                 480
Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
                515                 520                 525
Gly Gly Gln Gly Pro Tyr Gly Pro Gly Ala Ala Ser Ala Ala Val Ser
            530                 535                 540
Val Gly Gly Tyr Gly Pro Gln Ser Ser Val Pro Val Ala Ser Ala
545                 550                 555                 560
Val Ala Ser Arg Leu Ser Ser Pro Ala Ala Ser Ser Arg Val Ser Ser
                565                 570                 575
Ala Val Ser Ser Leu Val Ser Ser Gly Pro Thr Lys His Ala Ala Leu
            580                 585                 590
Ser Asn Thr Ile Ser Ser Val Val Ser Gln Val Ser Ala Ser Asn Pro
            595                 600                 605
Gly Leu Ser Gly Cys Asp Val Leu Val Gln Ala Leu Leu Glu Val Val
            610                 615                 620
Ser Ala Leu Val Ser Ile Leu Gly Ser Ser Ser Ile Gly Gln Ile Asn
625                 630                 635                 640
Tyr Gly Ala Ser Ala Gln Tyr Thr Gln Met Val Gly Gln Ser Val Ala
                645                 650                 655
Gln Ala Leu Ala
            660

<210> SEQ ID NO 3
<211> LENGTH: 1183
<212> TYPE: PRT
<213> ORGANISM: Artificial
<220> FEATURE:
<223> OTHER INFORMATION: ADF3Kai-Large

<400> SEQUENCE: 3

Met His His His His His His His His His Ser Ser Gly Ser Ser
1               5                   10                  15
Leu Glu Val Leu Phe Gln Gly Pro Ala Arg Ala Gly Ser Gly Gln Gln
                20                  25                  30
Gly Pro Gly Gln Gln Gly Pro Gly Gln Gln Gly Pro Gly Gln Gln Gly
            35                  40                  45
Pro Tyr Gly Pro Gly Ala Ser Ala Ala Ala Ala Ala Ala Gly Gly Tyr
        50                  55                  60
Gly Pro Gly Ser Gly Gln Gln Gly Pro Ser Gln Gln Gly Pro Gly Gln
65                  70                  75                  80
Gln Gly Pro Gly Gly Gln Gly Pro Tyr Gly Pro Gly Ala Ser Ala Ala
                85                  90                  95
Ala Ala Ala Ala Gly Gly Tyr Gly Pro Gly Ser Gly Gln Gln Gly Pro
            100                 105                 110
Gly Gly Gln Gly Pro Tyr Gly Pro Gly Ser Ser Ala Ala Ala Ala Ala
            115                 120                 125
Ala Gly Gly Asn Gly Pro Gly Ser Gly Gln Gln Gly Ala Gly Gln Gln
            130                 135                 140

```
Gly Pro Gly Gln Gln Gly Pro Gly Ala Ser Ala Ala Ala Ala Ala
145                 150                 155                 160
Gly Gly Tyr Gly Pro Gly Ser Gly Gln Gln Gly Pro Gly Gln Gln Gly
            165                 170                 175
Pro Gly Gly Gln Gly Pro Tyr Gly Pro Gly Ala Ser Ala Ala Ala
            180                 185                 190
Ala Ala Gly Gly Tyr Gly Pro Gly Ser Gly Gln Gln Gly Pro Gly Gln Gln
        195                 200                 205
Gly Pro Gly Gly Gln Gly Pro Tyr Gly Pro Gly Ala Ser Ala Ala Ala
        210                 215                 220
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gly Pro Tyr Gly
                245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gly Pro
            275                 280                 285
Tyr Gly Pro Gly Ala Ser Ala Ala Ser Ala Ala Ser Gly Gly Tyr Gly
        290                 295                 300
Pro Gly Ser Gly Gln Gln Gly Pro Gly Gln Gln Gly Pro Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
            340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Gly Tyr Gly Pro Gly
            370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Ala Gly Ala Ala Gly
            435                 440                 445
Gly Tyr Gly Pro Gly Ser Gly Gln Gln Gly Pro Gly Gln Gln Gly Pro
450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
            515                 520                 525
Gly Gly Gln Gly Pro Tyr Gly Pro Gly Ala Ala Ser Ala Ala Val Ser
            530                 535                 540
Val Ser Arg Ala Arg Ala Gly Ser Gly Gln Gln Gly Pro Gly Gln Gln
545                 550                 555                 560
```

```
Gly Pro Gly Gln Gln Gly Pro Gly Gln Gly Pro Tyr Gly Pro Gly
            565                 570                 575

Ala Ser Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gln Gln Gly
625                 630                 635                 640

Tyr Gly Pro Gly Ser Ser Ala Ala Ala Ala Ala Gly Gly Asn Gly
            645                 650                 655

Pro Gly Ser Gly Gln Gln Gly Ala Gly Gln Gln Gly Pro Gly Gln
            660                 665                 670

Gly Pro Gly Ala Ser Ala Ala Ala Ala Ala Gly Gly Tyr Gly Pro
            675                 680                 685

Gly Ser Gly Gln Gln Gly Pro Gly Gln Gln Gly Pro Gly Gln Gly
            690                 695                 700

Pro Tyr Gly Pro Gly Ala Ser Ala Ala Ala Ala Ala Gly Gly Tyr
705                 710                 715                 720

Gly Pro Gly Ser Gly Gln Pro Gly Gln Gln Gly Pro Gly Gly Gln
            725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro Gly
            755                 760                 765

Gln Gln Gly Pro Gly Gly Gln Gly Pro Tyr Gly Pro Gly Ala Ser Ala
            770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gln Gly Pro Tyr Gly Pro Gly Ala
            805                 810                 815

Ser Ala Ala Ser Ala Ala Ser Gly Gly Tyr Gly Pro Gly Ser Gly Gln
            820                 825                 830

Gln Gly Pro Gly Gln Gln Gly Pro Gly Gly Gln Gly Pro Tyr Gly Pro
            835                 840                 845

Gly Ala Ser Ala Ala Ala Ala Ala Gly Gly Tyr Gly Pro Gly Ser
            850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
            930                 935                 940

Gln Gln Gly Pro Gly Gln Gly Pro Gly Gly Gln Gly Ala Tyr Gly
945                 950                 955                 960

Pro Gly Ala Ser Ala Ala Ala Gly Ala Ala Gly Gly Tyr Gly Pro Gly
            965                 970                 975
```

-continued

Ser Gly Gln Gln Gly Pro Gly Gln Gln Gly Pro Gly Gln Gln Gly Pro
            980                 985                 990

Gly Gln Gln Gly Pro Gly Gln Gln Gly Pro Gly Gln Gln Gly Pro Gly
        995                 1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly
    1040                1045                1050

Gln Gly Pro Tyr Gly Pro Gly Ala Ala Ser Ala Ala Val Ser Val
    1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu Gly Ser Ser Ser
    1145                1150                1155

Ile Gly Gln Ile Asn Tyr Gly Ala Ser Ala Gln Tyr Thr Gln Met
    1160                1165                1170

Val Gly Gln Ser Val Ala Gln Ala Leu Ala
    1175                1180

<210> SEQ ID NO 4
<211> LENGTH: 24
<212> TYPE: PRT
<213> ORGANISM: Artificial
<220> FEATURE:
<223> OTHER INFORMATION: His tag and start codon

<400> SEQUENCE: 4

Met His His His His His His His His His Ser Ser Gly Ser Ser
1               5                   10                  15

Leu Glu Val Leu Phe Gln Gly Pro
            20

<210> SEQ ID NO 5
<211> LENGTH: 1983
<212> TYPE: DNA
<213> ORGANISM: Artificial
<220> FEATURE:
<223> OTHER INFORMATION: ADF3Kai

<400> SEQUENCE: 5
atgcatcacc atcatcatca tcaccaccac cattcctcgg gctcatcctt ggaagtgtta        60
tttcaaggac cagcacgagc cggttcggga caacaagggc ctggccagca gggcccaggt       120
caacaagggc caggacagca gggtccttat gggcccggcg caagcgcagc agctgcggcc       180
gctggtggct atggtcctgg ctccggtcaa cagggccctt cgcaacaagg tccggggcag       240
caaggtcctg gtggcagggg tcctacgggg ccggggggcga gtgcggcagc agccgctgca       300
ggcggttatg gtccaggaag cggacagcaa ggtccgggag gtcaaggtcc gtatggccca       360

```
ggctctagcg cggctgccgc tgccgcgggt ggcaacggac cagggagcgg acaacagggc    420
gcgggacaac agggtccagg acagcaaggc ccagggcgt cggcggctgc agcggcggcc    480
ggaggctatg acccggctc aggacaacag ggaccgggtc aacaaggacc cgtggccaa     540 ggcccctatg cccgggcgc cagcgcgcc gcagccgccg cgggcgggta cggcccggt      600 agcggccagg gaccaggtca gcaggggcca ggaggtcagg gcccatacgg tccgggcgca    660
tccgcggcgg cggcagcggc aggtggctac ggtcccggaa gcggccaaca ggggccaggg    720
caacaaggac caggacaaca aggtcctggg ggccaaggac cgtatggacc aggagcatca    780
gctgcagccg cggcagctgg cggttacggt ccaggctacg ccagcaggg tccgggtcag    840 cagggaccgg gaggccaggg gccttatggc cctggcgctt ccgcagccag tgccgcttct    900
ggaggatacg gccgggaag cggtcagcaa ggccctggcc aacaaggacc tggaggccaa    960
gggccctacg gcccaggagc ctcggcagcc gcagctgccg caggtgggta tgggccaggt    1020
agcgggcaac aagggccggg tcagcaagga ccggggcaac agggacctgg cagcaagga    1080 cccgggggtc aaggcccgta cggacctggt gcgtctgcag ctgctgctgc ggctggtgga    1140
tatggtccgg gatcggggca gcagggtccc ggtcagcagg gcctggtca gcaagggcca    1200 ggccaacagg gaccccgaca caaggcccg ggtcaacagg gtcctggaca gcaggggccg    1260
ggccaacaag gccctgggca cagggtccg gggggacagg gggcctatgg gcctggcgca    1320
tctgccgccg ctggcgcagc cggtgggtac gggcctgggt caggtcaaca ggggcctggt    1380
caacaaggcc ccgggcaaca gggcccggc cagcaaggtc cagggcagca gggccccgga    1440 cagcaaggc ctggacaaca ggggcccgga cagcaggac cttacgggcc cggtgcgagc    1500
gcagcggccg ccgccgcagg gggatatggc cccggatcgg gccagcaggg accaggccag    1560
caaggacctg gccaacaggg cccggggggt caggggccgt atggtccgg cgctgcaagt    1620 gctgcagtgt ccgttggagg ttacggccct cagtcttcgt ctgttccggt ggcgtccgca    1680
gttgcgagta actgtcttc acctgctgct tcatcgcgag tatcgagcgc tgtttcgtct    1740
cttgtctcgt cgggtcccac gaaacatgcc gccctttcaa atacgatttc atctgtagtg    1800
tcccaagtta gtgcaagtaa cccggggtta tccggatgcg acgttctcgt tcaggcactc    1860
ctagaagtag tatccgcgtt ggtgagcatc ttaggcagct cctcgatagg tcaaataaac    1920
tatggtgctt cagcccagta tacacagatg gtgggacaga gcgtcgcgca ggcattggct    1980
taa                                                                 1983

<210> SEQ ID NO 6
<211> LENGTH: 3552
<212> TYPE: DNA
<213> ORGANISM: Artificial
<220> FEATURE:
<223> OTHER INFORMATION: ADF3Kai-Large

<400> SEQUENCE: 6
atgcatcacc atcatcatca tcaccaccac cattcctcgg gctcatcctt ggaagtgtta     60
tttcaaggac cagcacgagc cggttcggga caacaagggc ctggccagca gggcccaggt    120
caacaagggc caggacagca gggtccttat gggcccggcg caagcgcagc agctgcggcc    180
gctggtggct atggtcctgg ctccggtcaa cagggcccct tcgcaacaag gtcccgggcag    240 caaggtcctg gtggccaggg tccctacggg ccggggggga gtgcggcagc agccgctgca    300
ggcggttatg gtccaggaag cggacagcaa ggtccgggag gtcaaggtcc gtatggccca    360
ggctctagcg cggctgccgc tgccgcgggt ggcaacggac cagggagcgg acaacagggc    420
```

```
gcgggacaac agggtccagg acagcaaggc ccaggggcgt cggcggctgc agcggcggcc    480
ggaggctatg gacccggctc aggacaacag ggaccgggtc aacaaggacc cggtggccaa    540 ggccctatg gcccgggcgc cagcgcggcc gcagccgccg cgggcgggta cggccccggt    600
agcggccagg gaccaggtca gcaggggcca ggaggtcagg gcccatacgg tccgggcgca    660
tccgcggcgg cggcagcggc aggtggctac ggtcccggaa gcggccaaca ggggccaggg    720
caacaaggac caggacaaca aggtcctggg ggccaaggac cgtatggacc aggagcatca    780
gctgcagccg cggcagctgg cggttacggt ccaggctacg gccagcaggg tccgggtcag    840
cagggaccgg gaggccaggg gccttatggc cctggcgctt ccgcagccag tgccgcttct    900
ggaggatacg ggccgggaag cggtcagcaa ggccctggcc aacaaggacc tggaggccaa    960
gggccctacg gcccaggagc ctcggcagcc gcagctgccg caggtgggta tgggccaggt   1020
agcgggcaac aagggccggg tcagcaagga ccggggcaac agggacctgg gcagcaagga   1080
cccgggggtc aaggcccgta cggacctggt gcgtctgcag ctgctgctgc ggctggtgga   1140
tatggtccgg gatcggggca gcaggtcccc ggtcagcagg gcctggtca gcaagggcca   1200 ggccaacagg gacccggaca caaggcccg gtcaacagg gtcctggaca gcaggggccg   1260
ggccaacaag gccctgggca cagggtccg ggggacagg gggcctatgg gcctggcgca   1320
tctgccgccg ctggcgcagc cggtgggtac gggcctgggt caggtcaaca ggggcctggt   1380
caacaaggcc ccgggcaaca gggccccggc cagcaaggtc cagggcagca gggccccgga   1440
cagcaagggc ctggacaaca ggggcccgga cagcagggac cttacgggcc cggtgcgagc   1500
gcagcggccg ccgccgcagg gggatatggc cccggatcgg ccagcaggg accaggccag   1560 caaggacctg gccaacaggg cccggggggt caggggccgt atggtcccgg cgctgcaagt   1620
gctgcagtgt ccgtttctag agcacgagc ggttcgggac aacaagggcc tggccagcag   1680
ggcccaggtc aacaagggcc aggacagcag ggtccttatg ggcccggcgc aagcgcagca   1740
gctgcggccg ctggtggcta tggtcctggc tccggtcaac agggcccttc gcaacaaggt   1800
cccgggcagc aaggtcctgg tggccaggt ccctacgggc cggggcgag tgcggcagca   1860 gccgctgcag gcggtttatgg tccaggaagc ggacagcaag gtccgggagg tcaaggtccg   1920
tatggcccag gctctagcgc ggctgccgct gccgcgggtg gcaacggacc agggagcgga   1980
caacagggcg cgggacaaca gggtccagga cagcaaggcc caggggcgtc ggcggctgca   2040
gcggcggccg gaggctatgg acccggctca ggacaacagg gaccgggtca caaggaccc   2100 ggtggccaag gccctatgg cccgggcgc agcgcggccg cagccgccgc gggcgggtac   2160
ggccccggta gcggccaggg accaggtcag caggggccag gaggtcaggg cccatacggt   2220
ccgggcgcat ccgcggcggc ggcagcggca ggtggctacg gtcccggaag cggccaacag   2280
gggccagggc aacaaggacc aggacaacaa ggtcctgggg gccaaggacc gtatggacca   2340
ggagcatcag ctgcagccgc ggcagctggc ggttacggtc aggctacgg ccagcagggt   2400 ccgggtcagc agggaccggg aggccagggg ccttatggcc ctggcgcttc cgcagccagt   2460
gccgcttctg gaggatacgg gccgggaagc ggtcagcaag gccctggcca acaaggacct   2520
ggaggccaag ggccctacgg cccaggagcc tcggcagccg cagctgccgc aggtgggtat   2580
gggccaggta gcgggcaaca agggccgggt cagcaaggac cggggcaaca gggacctggg   2640
cagcaaggac ccgggggtca aggcccgtac ggacctggtg cgtctgcagc tgctgctgcg   2700
gctggtggat atggtccggg atcggggcag cagggtcccg gtcagcaggg ccctggtcag   2760
caagggccag gccaacaggg acccggacaa caaggcccgg tcaacaggg tcctggacag   2820
```

| | |
|---|---|
| caggggccgg gccaacaagg ccctgggcaa cagggtccgg ggggacaggg ggcctatggg | 2880 |
| cctggcgcat ctgccgccgc tggcgcagcc ggtgggtacg ggcctgggtc aggtcaacag | 2940 |
| gggcctggtc aacaaggccc cgggcaacag ggccccggcc agcaaggtcc agggcagcag | 3000 |
| ggcccgggac agcaagggcc tggacaacag ggggcccgga c agcagggacc ttacgggccc | 3060 |
| ggtgcgagcg cagcggccgc cgccgcaggg ggatatggcc ccggatcggg ccagcaggga | 3120 |
| ccaggccagc aaggacctgg ccaacagggc ccgggggtc aggggccgta tggtcccggc | 3180 |
| gctgcaagtg ctgcagtgtc cgttggaggt tacggccctc agtcttcgtc tgttccggtg | 3240 |
| gcgtccgcag ttgcgagtag actgtcttca cctgctgctt catcgcgagt atcgagcgct | 3300 |
| gtttcgtctc ttgtctcgtc gggtcccacg aaacatgccg ccctttcaaa tacgatttca | 3360 |
| tctgtagtgt cccaagttag tgcaagtaac ccggggttat ccggatgcga cgttctcgtt | 3420 |
| caggcactcc tagaagtagt atccgcgttg gtgagcatct taggcagctc ctcgataggt | 3480 |
| caaataaact atggtgcttc agcccagtat acacagatgg tgggacagag cgtcgcgcag | 3540 |
| gcattggctt aa | 3552 |

<210> SEQ ID NO 7
<211> LENGTH: 3465
<212> TYPE: DNA
<213> ORGANISM: Artificial
<220> FEATURE:
<223> OTHER INFORMATION: ADF3Kai-Large-NRSH1

<400> SEQUENCE: 7

| | |
|---|---|
| atgcatcacc atcatcatca tcaccaccac cattcctcgg gctcatcctt ggaagtgtta | 60 |
| tttcaaggac cagcacgagc cggttcggga caacaagggc ctggccagca gggcccaggt | 120 |
| caacaagggc caggacagca gggtccttat gggcccggcg caagcgcagc agctgcggcc | 180 |
| gctggtggct atggtcctgg ctccggtcaa cagggccctt cgcaacaagg tcccgggcag | 240 |
| caaggtcctg gtggccaggg tccctacggg cggggggcga gtgcggcagc agccgctgca | 300 |
| ggcggttatg gtccaggaag cggacagcaa ggtccgggag gtcaaggtcc gtatggccca | 360 |
| ggctctagcg cggctgccgc tgccgcgggt ggcaacggac cagggagcgg acaacagggc | 420 |
| gcgggacaac agggtccagg acagcaaggc ccaggggcgt cggcggctgc agcggcggcc | 480 |
| ggaggctatg gacccggctc aggacaacag ggaccgggtc aacaaggacc cgtggccaa | 540 |
| ggcccctatg gcccgggcgc cagcgcggcc gcagccgccg cggcgggta cggccccggt | 600 |
| agcggccagg gaccaggtca gcagggggcca ggaggtcagg gcccatacgg tccgggcgca | 660 |
| tccgcggcgg cggcagcggc aggtggctac ggtcccggaa gcggccaaca ggggccaggg | 720 |
| caacaaggac caggacaaca aggtcctggg ggccaaggac cgtatggacc aggagcatca | 780 |
| gctgcagccg cggcagctgg cggttacggt ccaggctacg gccagcaggg tccgggtcag | 840 |
| cagggaccgg gaggccaggg gccttatggc cctggcgctt ccgcagccag tgccgcttct | 900 |
| ggaggatacg ggcgggaag cggtcagcaa ggccctggcc aacaaggacc tggaggccaa | 960 |
| gggccctacg gccaggagc ctcggcagcc gcagctgccg caggtgggta tgggccaggt | 1020 |
| agcgggcaac aagggccggg tcagcaagga ccggggcaac agggacctgg cagcaagga | 1080 |
| cccgggggtc aaggcccgta cggacctggt gcgtctgcag ctgctgctgc ggctggtgga | 1140 |
| tatggtccgg gatcggggca gcagggtccc ggtcagcagg gcctggtca gcaagggcca | 1200 |
| ggccaacagg gacccggaca acaaggcccg ggtcaacagg gtcctggaca gcagggccgg | 1260 |
| ggccaacaag gccctgggca cagggtccg gggggacagg gggcctggg gcctggcgca | 1320 |

```
tctgccgccg ctggcgcagc cggtgggtac gggcctgggt caggtcaaca ggggcctggt      1380
caacaaggcc ccgggcaaca ggccccggc cagcaaggtc cagggcagca gggcccggga       1440
cagcaagggc ctggacaaca ggggcccgga cagcagggac cttacgggcc cggtgcgagc      1500
gcagcggccg ccgccgcagg gggatatggc cccggatcgg ccagcaggg accaggccag       1560
caaggacctg gccaacaggg cccgggggt cagggccgt atggtcccgg cgctgcaagt        1620
gctgcagtgt ccgttttctag agcacgagcc ggttcgggac aacaagggcc tggccagcag    1680
ggcccaggtc aacaagggcc aggacagcag ggtccttatg ggcccggcgc aagcgcagca     1740
gctgcggccg ctggtggcta tggtcctggc tccggtcaac agggcccttc gcaacaaggt     1800
cccgggcagc aaggtcctgg tggccaggt ccctacgggc cggggcgag tgcggcagca       1860
gccgctgcag gcggttatgg tccaggaagc ggacagcaag gtccgggagg tcaaggtccg      1920
tatgcccag gctctagcgc ggctgccgct ccgcgggtg caacggacc agggagcgga        1980
caacagggcg cgggacaaca gggtccagga cagcaaggcc caggggcgtc ggcggctgca     2040
gcggcggccg gaggctatgg acccggctca ggacaacagg gaccgggtca acaaggaccc     2100
ggtggccaag gcccctatgg cccgggcgcc agcgcggccg cagccgccgc gggcgggtac     2160
ggccccggta gcgccaggg accaggtcag caggggccag gaggtcaggg cccatacggt      2220
ccgggcgcat ccgcgcggc ggcagcggca ggtggctacg gtcccggaag cggccaacag      2280
gggccagggc aacaaggacc aggacaacaa ggtcctgggg gccaaggacc gtatggacca    2340
ggagcatcag ctgcagccgc ggcagctggc ggttacggtc caggctacgg ccagcagggt    2400
ccgggtcagc agggaccggg aggccagggg cctatggcc ctggcgcttc cgcagccagt     2460
gccgcttctg gaggatacgg gccgggaagc ggtcagcaag gccctggcca acaaggacct    2520
ggaggccaag ggccctacgg cccaggagcc tcggcagccg cagctgccgc aggtgggtat    2580
ggccaggta gcgggcaaca agggccgggt cagcaaggac cggggcaaca gggacctggg      2640
cagcaaggac ccgggggtca aggcccgtac ggacctggtg cgtctgcagc tgctgctgcg    2700
gctggtggat atggtccggg atcggggcag caggtcccg gtcagcaggg ccctggtcag    2760
caagggccag gccaacaggg acccggacaa caaggcccgg gtcaacaggg tcctggacag    2820
caggggccgg gccaacaagg ccctgggcaa cagggtccgg ggggacaggg ggcctatggg    2880
cctgcgcat ctgccgccgc tggcgcagcc ggtgggtacg ggcctgggtc aggtcaacag     2940
gggcctggtc aacaaggccc cggcaacag ggccccggcc agcaaggtcc agggcagcag    3000
ggcccgggac agcaagggcc tggacaacag gggcccggac agcagggacc ttacgggccc    3060
ggtgcgagcg cagcggccgc cgccgcaggg ggatatggcc ccggatcggg ccagcaggga    3120
ccaggccagc aaggacctgg ccaacagggc cgggggggtc agggccgta tggtcccggc     3180
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gttcgtctc ttgtctcgtc gggtcccacg aaacatgccg cccttcaaa tacgatttca     3360
tctgtagtgt cccaagttag tgcaagtaac ccggggttat ccggatgcga cgttctcgtt    3420
caggcactcc tagaagtagt atccgcgttg gtgagcatct tataa                    3465
```

<210> SEQ ID NO 8
<211> LENGTH: 20
<212> TYPE: DNA
<213> ORGANISM: Artificial
<220> FEATURE:
<223> OTHER INFORMATION: T7 promoter primer

```
<400> SEQUENCE: 8
taatacgact cactataggg                                              20

<210> SEQ ID NO 9
<211> LENGTH: 27
<212> TYPE: DNA
<213> ORGANISM: Artificial
<220> FEATURE:
<223> OTHER INFORMATION: Rep Xba I primer

<400> SEQUENCE: 9
tctagaaacg gacactgcag cacttgc                                      27

<210> SEQ ID NO 10
<211> LENGTH: 28
<212> TYPE: DNA
<213> ORGANISM: Artificial
<220> FEATURE:
<223> OTHER INFORMATION: Xba I Rep primer

<400> SEQUENCE: 10
tctagagcac gagccggttc gggacaac                                     28

<210> SEQ ID NO 11
<211> LENGTH: 19
<212> TYPE: DNA
<213> ORGANISM: Artificial
<220> FEATURE:
<223> OTHER INFORMATION: T7 terminator primer

<400> SEQUENCE: 11
gctagttatt gctcagcgg                                               19

<210> SEQ ID NO 12
<211> LENGTH: 5
<212> TYPE: PRT
<213> ORGANISM: Artificial
<220> FEATURE:
<223> OTHER INFORMATION: REP6-U1
<220> FEATURE:
<221> NAME/KEY: UNSURE
<222> LOCATION: (1)..(5)
<223> OTHER INFORMATION: Xaa at position 4 or 5 is any one of amino
      acids, in particular, it preferably is Ala, Ser, Tyr, Gln, Val,
      Leu or Ile, it more preferably is Ala, Ser, Tyr, Gln or Val.

<400> SEQUENCE: 12

Gly Pro Gly Xaa Xaa
1               5

<210> SEQ ID NO 13
<211> LENGTH: 5
<212> TYPE: PRT
<213> ORGANISM: Artificial
<220> FEATURE:
<223> OTHER INFORMATION: REP6-U2
<220> FEATURE:
<221> NAME/KEY: UNSURE
<222> LOCATION: (1)..(5)
<223> OTHER INFORMATION: Xaa at position 5 is any one of amino acids,
      in particular, it preferably is Ala, Ser, Tyr, Gln, Val, Leu or
      Ile, it more preferably is Ala, Ser, Tyr, Gln or Val.

<400> SEQUENCE: 13

Gly Pro Gly Gly Xaa
1               5
```